United States Patent [19]
Li et al.

[11] Patent Number: 5,763,280
[45] Date of Patent: Jun. 9, 1998

[54] CYANIDE-FREE LYTIC REAGENT COMPOSITION AND METHOD FOR HEMOGLOBIN AND CELL ANALYSIS

[75] Inventors: Yi Li; Carole Young, both of Miami, Fla.

[73] Assignee: Coulter International Corp., Miami, Fla.

[21] Appl. No.: 786,505

[22] Filed: Jan. 21, 1997

[51] Int. Cl.⁶ .................................................. G01N 33/72
[52] U.S. Cl. .................... 436/66; 436/8; 436/10; 436/15; 436/17; 436/18; 436/63; 436/166; 436/175; 435/2; 252/408.1; 424/93.71; 424/93.73; 424/529; 424/533; 424/534
[58] Field of Search .................... 436/8, 10, 15, 436/16, 17, 18, 63, 66, 164, 166, 174, 175, 176; 435/2; 252/408.1; 424/93.71, 93.73, 529–534

[56] References Cited

U.S. PATENT DOCUMENTS

| | | | |
|---|---|---|---|
| 4,185,964 | 1/1980 | Lancaster | 436/17 |
| 4,485,175 | 11/1984 | Ledis et al. | 436/63 |
| 5,242,832 | 9/1993 | Sakata | 436/17 |
| 5,250,437 | 10/1993 | Toda et al. | 436/10 |
| 5,612,223 | 3/1997 | Kim et al. | 436/17 |
| 5,686,308 | 11/1997 | Li et al. | 436/63 |

FOREIGN PATENT DOCUMENTS

WO9524651 9/1995 WIPO.

OTHER PUBLICATIONS

Oshiro, Iwao et al. "New Method for Hemoglobin Determination by Using Sodium Lauryl Sulfate (SLS)." Clin. Biochem. 15 (1) 83–88 (1982).

*Primary Examiner*—Maureen M. Wallenhorst
*Attorney, Agent, or Firm*—Mitchell E. Alter

[57] ABSTRACT

A cyanide-free lytic reagent composition and method for measuring the total hemoglobin concentration in a blood sample, for counting the number of leukocytes and for deferential counting of three leukocyte subpopulations including lymphocytes, monocytes, and granulocytes are described. The cyanide-free lytic reagent composition includes a hemolytic surfactant chosen from quaternary ammonium salts, pyridinium salts, organic phosphate esters, and alkyl sulfonates to lyse erythrocytes and release hemoglobin, and an organic ligand chosen from triazole and its derivatives, tetrazole and its derivatives, alkaline metal salts of oxonic acid, melamine, aniline-2-sulfonic acid, quinaldic acid, 2-amino-1,3,4-thiadiazole, triazine and its derivatives, urazole, DL-pipecolinic acid, isonicotinamide, anthranilonitrile, 6-aza-2-thiothymine, adenine, 3-(2-thienyl)acrylic acid, benzoic acid and alkali metal and ammonium salts of benzoic acid, and pyrazine and its derivatives to form a stable chromogen with hemoglobin. The lytic reagent composition has a pH ranging from about 1 to about 13. The lytic reagent composition is mixed with a blood sample which is prediluted with a suitable blood diluent and the UV absorption of the sample mixture is measured at the predetermined absorption wavelength of the formed chromogen from 510 nm to 560 nm. Counting the numbers of leukocytes and differential counting of three leukocyte subpopulations are accomplished simultaneously on an automated cell counter utilizing DC impedance measurement. Alternatively, the organic ligands can be added to a suitable blood diluent for hemoglobin and leukocyte analysis.

24 Claims, 12 Drawing Sheets

CYANIDE-FREE LYTIC REAGENT COMPOSITION AND METHOD FOR HEMOGLOBIN AND CELL ANALYSIS

BACKGROUND OF THE INVENTION

1. Field of the Invention

The present invention relates to lytic reagent compositions, diluents and methods for use in measuring total hemoglobin concentration in a blood sample, either manually or automatically, and for use in combination with a simultaneous leukocyte counting or differential counting of leukocyte subpopulations.

2. Disscussion of the Prior Art

The determination of total hemoglobin is indicative of the oxygen-carrying capacity of whole blood. More than 300 abnormal hemoglobins have been discovered upon examination of patients with clinical symptoms and by electrophoretic surveys of a clinically normal population. Many of these abnormalities result in clinical pathologies having altered hemoglobin levels or hemoglobin having an altered ability to bind oxygen. Among these diseases are sickle cell anemia, both α and β-thalassemias and hemoglobin M.

An ability to measure hemoglobin (Hgb) in blood samples is an essential part of diagnostic analysis and is also important for monitoring responsiveness to therapies directed towards diseases which affect hemoglobin and to therapies which are directed towards other diseases but which may have adverse side effects on the hemoglobin level.

Leukocytes in the peripheral blood of normal subjects consist of five types, i.e., lymphocytes, monocytes, neutrophils, eosinophils and basophils. The latter three types of leukocytes are collectively referred to as granulocytes. Different types of leukocytes have different biological functionalities. Counting and differentiating different types of leukocytes in a blood sample provides valuable information for clinical diagnosis. For instance, an increased number of monocyte occurs either during the convalescence period of patients suffering from infectious diseases or in such diseases as monocytic leukemia.

The classification and counting of leukocytes has most commonly been conducted by the differential counting method which is also referred to the manual method. Automatic blood analyzers are also commonly used for counting leukocytes, which employs a hemolytic reagent to lyse erythrocytes and prepares a sample only containing leukocytes. The sample mixture then is analyzed by impedance method. A more sophisticated apparatus has been developed that counts different types of leukocytes (differential counting) including monocytes, lymphocytes and granulocytes. Ideally, one would like to be able to accomplish multiple diagnostic analyses such as hemoglobin measurement and counting the numbers of leukocytes or differential counting of leukocyte subpopulations in a single automated step.

Among the many well known methods for hemoglobin determination, the cyanide hemoglobin method has been recommended as a standard by the International Committee for Standardization in Hematology. Modification of this method by Matsubara and Okuzono has led to its wide usage in clinical laboratories. In this method, the iron ion of heme group in all forms of hemoglobin of the red cells are oxidized to methemoglobin by potassium ferricyanide. The methemoglobin is then complexed with cyanide anion, which has a very high affinity to iron ion of the heme group, to form a cyanmethemoglobin chromogen. This extremely stable chromogen has a maximum absorption at 540 nm, which is measured manually by UV spectrometry.

Despite of the stable chromogens formed by the standard cyanmethemoglobin method and its modified automatic methods, however, because of the potassium cyanide used, the reagent waste has caused enormous environmental concern. In last ten years, a tremendous effort has been given to develop automated hemoglobin analysis methods without utilizing cyanide.

Oshiro et al. *Clin. Biochem.* 1583 (1982), teach the use of a reagent for hemoglobin analysis which comprises sodium laurylsulfate (SLS) and Triton X-100 (a nonionic surfactant) in a neutral pH (7.2). The SLS is used to lyse erythrocytes and is believed to further produce a SLS-hemoglobin complex which has a maximum absorption at 539 nm and a shoulder at 572 nm. The reaction completes within 5–10 minutes and the total hemoglobin measurement is quantitative. However, as later explained in U.S. Pat. No. 5,242,832 (to Sakata), it is not possible with Oshiro's method to analyze leukocytes simultaneously with hemoglobin measurement.

U.S. Pat. No. 5,242,832 (to Sakata) discloses a cyanide-free lysing reagent for counting leukocytes and measuring the hemoglobin concentration in blood samples. The lysing reagent comprises at least one first surfactant which is a quaternary ammonium salt, at least one second surfactant which includes cationic and amphoteric surfactants, and at least one hemoglobin stabilizer selected from the group including Tiron, 8-hydroxyquinoline, bipyridine, 1-10-phenanthroline, phenolic compounds, bisphenol, pyrazole and derivatives, second phenyl 5-pyrazolone and derivatives, phenyl 3-pyrazolone, and imidazole and derivatives. Sakata teaches that fractionation of the leukocytes into two or three groups including an aggregate of lymphocytes, an aggregate of monocytes, eosinophils and basophils, and an aggregate of neutrophils can only be accomplished by using at least two suitable surfactants and by rigorously controlling the surfactant concentration. Sakata also teaches that the preferred pH range of the lysing reagent is from 5.0 to 8.0. If the pH value is 3.0 or less, damage to the leukocytes increases thus rendering measurement of leukocytes difficult, and if the pH is 9.0 or more, the stability of hemoglobin deteriorates over time.

PCT/US95/02897 (Kim) discloses a cyanide-free method and reagent for determining hemoglobin in a whole blood sample. The reagent comprises a ligand selected from the group consisting of imidazole and derivatives, N-hydroxyacetamide, H-hydroxylamine, pyridine, oxazole, thiazole, pyrazole, pyrimidine, purine, quinoline and isoquinoline, and a surfactant with a strong erythrolytic capability selected from the group consisting of lauryl dimethylamine oxide and octylphenoxy polyethoxyethanol. The analysis method is fast, less than 10 seconds. However, the reagent only performs under an extreme alkaline condition, pH from 11 to 14. In addition, no capability of counting leukocytes or differentiating leukocyte subpopulations is taught by Kim.

None of above cyanide-free hemoglobin measurement methods are capable to provide the monocytes and total granulocyte counts simultaneously with the hemoglobin measurement; however, both parameters are valuable tools for clinical diagnosis of various diseases. A need arises for a more versatile cyanide-free hemoglobin measurement method and a multifunctional reagent which is capable to accomplish multiple diagnostic analyses in a single automated step.

SUMMARY OF THE INVENTION

In view of the foregoing discussions, an object of this invention is to provide a cyanide-free lytic reagent composition for measuring the total hemoglobin concentration present in a blood sample.

The cyanide-free lytic reagent composition comprises an aqueous solution of at least one surfactant in a sufficient amount to be able to hemolyse erythrocytes and release hemoglobin selected from the group consisting of quaternary ammonium salts, pyridinium salts, alkyl sulfonic acid, or alkaline metal salts of alkyl sulfonates, and organic phosphate esters, or alkaline metal salts of organic phosphate esters; and an organic ligand in a sufficient amount to form a stable chromogen with hemoglobin selected from the group consisting of triazole and its derivatives, tetrazole and its derivatives, alkaline metal salts of oxonic acid, melamine, aniline-2-sulfonic acid, quinaldic acid, 2-amino-1,3,4-thiadiazole, triazine and its derivatives, urazole, DL-pipecolinic acid, isonicotinamide, anthranilonitrile, 6-aza-2-thiothymine, adenine, 3-(2-thienyl)acrylic acid, benzoic acid and alkali metal and ammonium salts of benzoic acid, and pyrazine and its derivatives. The lytic reagent composition has a pH ranging from about 1 to about 13.

In a preferred mode, a combination of a quarternary ammonium salt or salts with an organic ligand disclosed is used to provide the measurement of total hemoglobin concentration and counting the numbers of leukocytes in a blood sample simultaneously by a DC impedance measurement method.

In the most preferred mode, a combination of a quarternary ammonium salt or salts with an organic ligand which is compatible with leukocyte differential analysis is used to provide the measurement of total hemoglobin concentration, counting the numbers of leukocytes and differential counting the leukocyte subpopulations of a blood sample simultaneously, wherein the leukocytes are differentiated into three subpopulations including lymphocytes, monocytes and granulocytes.

As will be better appreciated from the ensuing Detailed Description of Preferred Embodiments, the invention is particularly advantageous as compared to the prior art in that it provides a cyanide-free lytic reagent for hemoglobin measurement in a broad pH range.

Another object of the invention is to provide a method of using the lytic reagent composition with a suitable blood diluent for measuring the hemoglobin concentration of a blood, or in combination with a simultaneous counting of leukocyte numbers or differential counting of leukocyte subpopulations.

In one aspect, the method comprises diluting a blood sample with a suitable blood diluent, mixing a sufficient amount of lytic reagent composition with the diluted sample, then measuring the sample photometrically at a predetermined wavelength for hemoglobin concentration and at the same time counting the numbers of leukocytes or differential counting the leukocyte subpopulations on a blood analyzer equipped with a DC impedance measurement device.

Alternatively, an organic ligand disclosed can also be added into a suitable blood diluent to form a stable hemoglobin chromogen when used in combination with a lytic reagent. In a further aspect, the present invention provides a blood diluent and a method of using the same for hemoglobin measurement as well as for counting the numbers of leukocytes and differential counting of leukocyte subpopulations. Another important advantage of this invention is that it provides designers a flexibility on utilizing hemoglobin ligands in either a lytic reagent or a diluent depending upon specific product requirements.

The invention and its various advantages will be better understood from the ensuing description of preferred embodiments, reference being made to the accompanying drawings.

DETAILED DESCRIPTION OF PREFERRED EMBODIMENTS

Figure 1A:
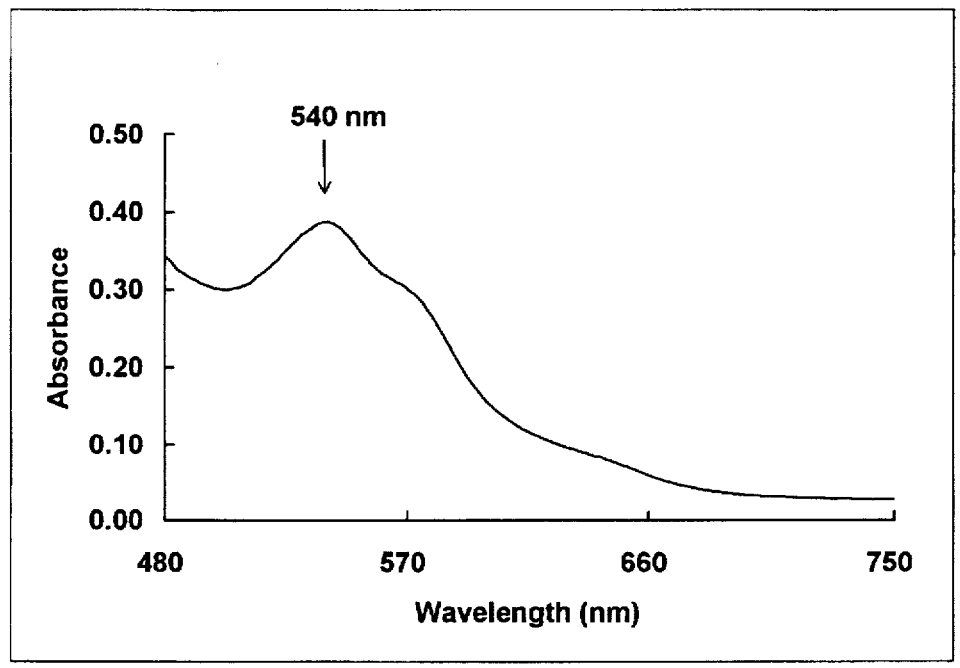
FIGS. 1a and 1b are the absorption spectra of whole blood samples processed according to the procedure described in Example 1 using the lytic reagent compositions of Example 1 of the present invention (formula 1b and 1c).

In general, to measure total hemoglobin concentration in a blood sample photometrically it is necessary to lyse erythrocytes and release hemoglobin using a hemolytic reagent, then to convert the hemoglobin to a stable chromogen which is able to be detected and measured by UV spectroscopy at a predetermined wavelength. For the measurement to be quantitative and accurate, the formed chromogen needs to be stable, at least stable in the time frame of the measurement. Lysis of erythrocytes can be accomplished by acid lysing, osmotic lysing and utilizing various natural and synthetic surfactants. The released hemoglobin comprises various forms, such as oxyhemoglobin, deoxyhemoglobin, methemoglobin, carboxyhemoglobin and etc.

The most efficient method to convert hemoglobin to a stable chromogen is to provide a ligand which has a high affinity to the heme iron to form a stable hemoglobin complex. This has been successfully demonstrated by the cyanmethemoglobin method, wherein the cyanide anion has an extremely high affinity to the heme iron. The terms of hemoglobin complex and hemoglobin chromogen are used interchangeably in this context. Usually, in the absence of a high affinity ligand, the formed hemoglobin chromogen is not very stable. It's absorption varies, and in most cases decays with time. Under this condition, the method of analysis is unreliable even if the kinetics of the decomposition reaction is well monitored and corrected because the chromogen could be very sensitive to the environment such as temperature and sample preparation conditions, etc. When an appropriate hemoglobin ligand is provided, the hemoglobin conversion can be quantitative, and the reliability of the analysis method is ensured by the stability of the formed hemoglobin complex.

Selection of a ligand depends on the analysis to be accomplished, for instance, for hemoglobin measurement only, or for a multiple diagnostic analysis such as counting the numbers of leukocytes or differential counting of leukocyte subpopulations in combination with the hemoglobin measurement. A ligand which is perfect for hemoglobin measurement may not be suitable for the later applications if the ligand is not compatible to the other analyses. An example taught by Sakata (in U.S. Pat. No. 5,242,832) is that SLS used for lysing erythrocytes and forming Hgb-SLS chromogen can not be used for leukocyte measurement.

The present invention is directed to a cyanide-free lytic reagent composition for measuring the total hemoglobin concentration present in a blood sample, or in combination with a simultaneous counting of the numbers of leukocytes or differential counting of leukocyte subpopulations. The cyanide-free lytic reagent composition comprises an aqueous solution of:

(I) at least one surfactant in a sufficient amount to be able to hemolyse erythrocytes and release hemoglobin selected from the group consisting of quaternary ammonium salts, represented by following molecular structure:

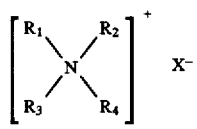

wherein
$R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride and bromide anions;

pyridinium salts represented by following molecular structure:

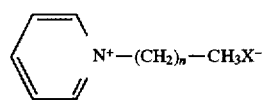

wherein n is an integer from 7 to 12 and $X^-$ is an anionic group;

alkyl sulfonic acid, or alkaline metal salts of alkyl sulfonates;

organic phosphate esters, or alkaline metal salts of organic phosphate esters;

(II) an organic ligand in a sufficient amount to form a stable chromogen with hemoglobin selected from the group consisting of:

(a) triazole such as 1,2,3-triazole and 1,2,4-triazole, and triazole derivatives such as 1,2,4-triazole-3-thiol, 1,2,4-triazole sodium derivative, triazole dicarboxylic acid and heteracyclic derivatives of triazole;

(b) tetrazole and its derivatives such as 5-amino tetrazole;

(c) alkaline metal salts of oxonic acid

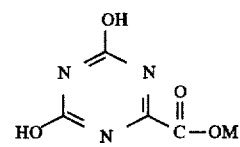

wherein M is an alkaline metal cation;

(d) melamine

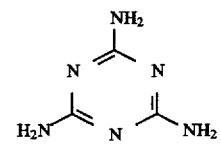

(e) aniline-2-sulfonic acid

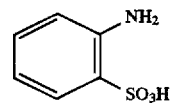

(f) quinaldic acid

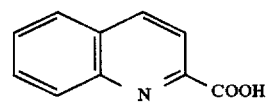

(g) 2-amino-1,3,4-thiadiazole

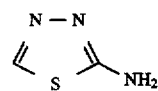

(h) triazine and its derivatives

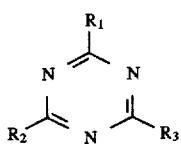

wherein $R_1$, $R_2$ and $R_3$ are —H, —OH, —SH, —COOH and heterocyclic derivatives of triazine;

(i) urazole

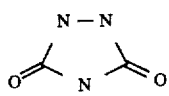

(j) DL-pipecolinic acid

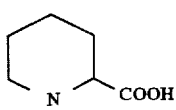

(k) isonicotinamide

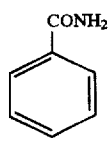

(l) anthranilonitrile

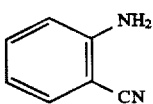

(m) 6-aza-2-thiothymine

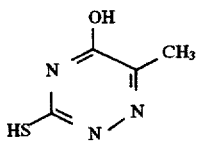

(n) adenine

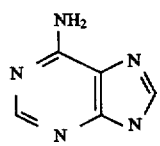

(o) 3-(2-thienyl)acrylic acid

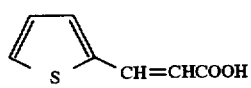

(p) benzoic acid, and alkali metal and ammonium salts of benzoic acid

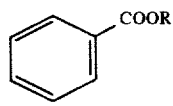

wherein R is —H, $NH_4^+$ and alkali metal cations;

(q) pyrazine and its derivatives

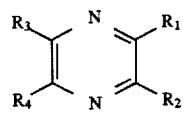

wherein $R_1$, $R_2$ $R_3$ and $R_4$ are —H, —CN, —OH, —SH, —COOH, —CONH$_2$.

The pH of the lytic reagent composition ranges from 1 to 13.

Among the hemolytic surfactants, quaternary ammonium salts are more preferred. The concentration of the surfactant in the lytic reagent composition needs to be in an amount sufficient to lyse erythrocytes and release hemoglobin while preserving leukocyte nuclear volumes. To count leukocytes, one does not need to keep the leukocyte membrane intact. In general, using the hemolytic surfactants described above in the lytic reagent composition of the present invention when erythrocytes are completely lysed and destructed, leukocyte membranes are partially lysed. It is the remaining nuclei of the leukocytes that enable the counting of leukocyte numbers and differentiation of leukocyte subpopulations into lymphocytes, monocytes and granulocytes using the DC impedance method. The concentration of the surfactants in the lytic reagent composition ranges from about 2 g/L to about 250 g/L, preferably, from about 4 g/L to about 80 g/L.

The concentration of the organic ligand in the lytic reagent composition needs to be sufficient to form a stable hemoglobin chromogen. The concentration varies with the ligand type, depending on the affinity of the ligand to the hemoglobin. In general, if the amount of ligand in the lytic reagent composition is not sufficient, the formed hemoglobin chromogen could be unstable. The concentration of the organic ligand in the lytic reagent composition of the present invention has been found to be effective in a broad range from about 1 g/L to about 30 g/L, preferably from about 2 g/L to about 15 g/L.

The concentrations of the chemical ingredients in the lytic reagent composition are the concentrations under conditions in which the hemoglobin and leukocyte measurements are accomplished with the use of a suitable blood diluent for the convenience of using the conventional blood analyzers. However, the concentrations of the chemical ingredients can be changed depending upon the volume ratio between the lytic reagent composition and the diluent.

Moreover, if an instrument employs a single lytic reagent composition, without predilution by a blood diluent, one can reduce the concentrations of the chemical ingredients of the lytic reagent composition, and adjust the conductivity of the lytic reagent composition enabling its use for impedance measurements. The conductivity can be adjusted by addition of suitable amounts of alkaline metal salts. In this type of single reagent method, the concentrations of the chemical ingredients of the lytic reagent composition should be the same as the concentrations contained in the final sample mixture of the present invention, which include both a diluent and a lytic reagent composition.

Optional additives can also be included in the lytic reagent composition in concentrations that their presence is compatible with the primary functional components of the lytic reagent composition. Among these additives are preservatives which have anti-oxidant properties, to increase the shelf-life of the composition, and which have antimicrobial properties.

The present invention is also directed to a method of using the above described cyanide-free lytic reagent composition for measuring the total hemoglobin concentration present in a blood sample, or in combination with a simultaneous counting of the numbers of leukocytes or differential counting of leukocyte subpopulations.

An anti-coagulated blood sample is diluted by a suitable blood diluent, then a sufficient amount of lytic reagent composition described above is mixed with the diluted sample by manual or mechanical mixing. The dilution ratio of the blood is from about 125:1 to about 500:1, total reagent volume versus blood. The sample mixture is measured photometrically, 8 to 60 seconds after the addition of the lytic reagent composition, either on a UV spectrometer or on an automated blood analyzer equipped with a UV detector at a predetermined absorption wavelength for total hemoglobin measurement. The sample mixture can also be introduced to a blood analyzer equipped with a UV detector and a DC impedance measurement device to measure the hemoglobin concentration of the blood sample and to count the numbers of leukocytes, or to further differentiate the leukocyte subpopulations based on the population distribution histogram obtained. In the later case, the leukocytes are differentiated into three subpopulations, including lymphocytes, monocytes and granulocytes.

The detection methods used for the leukocyte counting by a blood analyzer equipped with a DC impedance measurement device are generally described in U.S. Pat. No. 2,656,508 (to Wallace H. Coulter) which is hereby incorporated by reference in its entirety. The method of differentiating leukocyte subpopulations utilizing DC impedance measurement is described in U.S. Pat. Nos. 4,485,175 and 4,528,274.

The organic ligands described above, for instance, triazole and melamine, not only form stable chromogens with hemoglobin, but also stabilize the leukocytes in the treated sample mixture. This leukocyte stabilization effect prevents the leukocytes from over lysing and nuclear shrinkage, facilitates the separation of the leukocyte subpopulations based on their nuclear volumes, and makes the differentiation of leukocytes into three subpopulations possible with a broad pH range. Example 4 illustrates such successful examples using leukocyte stabilizing ligands in the lytic reagent compositions of the present invention.

On the other hand, some of the organic ligands described above, for instance, aniline-2-sulfonic acid and quinaldic acid, exhibit an intermediate to strong impact on the nuclear size of leukocyte subpopulations. When these ligands are used for hemoglobin measurement, leukocyte subpopulations collapse into one or two clusters, rendering the leukocyte differentiation difficult. However, even with these ligands the leukocyte nuclear size remains far above the cellular debris of the sample after treated by the lytic reagent composition and above the detection threshold of the conventional DC impedance measurement devices, so that an accurate leukocyte count can be achieved conveniently on commercial blood analyzers as illustrated by the applications in Example 3.

In general, the lytic reagent composition of the present invention comprising the organic ligands and surfactants described above is capable of measuring total hemoglobin concentration of a blood sample in a very broad pH range. Preferably, a combination of a quarternary ammonium salt or salts with any of the organic ligands is used to provide the measurement of total hemoglobin concentration and counting the numbers of leukocytes in a blood sample simultaneously by a DC impedance measurement method. Most preferably, a combination of a quarternary ammonium salt or salts with an organic ligand which is compatible with leukocyte differential analysis is used to provide the measurement of total hemoglobin concentration, counting the numbers of leukocytes and differential counting the leukocyte subpopulations of a blood sample simultaneously. In the most preferred mode, the leukocytes are differentiated into three subpopulations including lymphocytes, monocytes and granulocytes.

The cyanide-free lytic reagent composition and the method of using the same provide several advantages over the methods of hemoglobin measurement of the prior art. The present invention allows for an accurate measurement of hemoglobin concentration of a blood sample in the absence of cyanide along with a determination of total leukocyte numbers or differentiation of leukocyte subpopulations into lymphocytes, monocytes and granulocytes. The lytic reagent composition converts the hemoglobin present in a blood sample rapidly to a stable chromogen, from about 8 seconds to 60 seconds depending on the organic ligand and diluent used, allowing for rapid automated analysis. The hemoglobin chromogen once formed is stable during the time of measurement.

Figure 2:
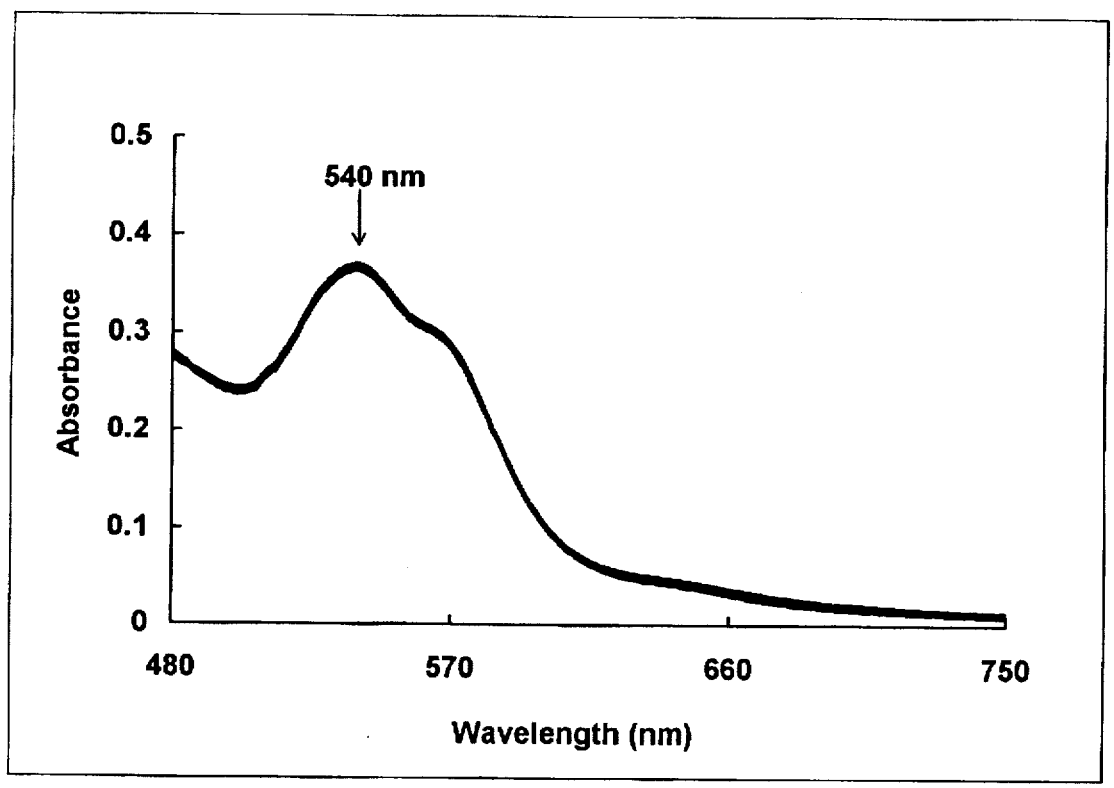
FIG. 2 shows a series of absorption spectra of a blood sample processed according to the procedure of Example 1 using the lytic reagent composition of formula 1a. Total of twelve spectra were acquired in twelve hours with a one hour interval.

FIG. 2 shows a series of absorption spectra of a blood sample processed according to the procedure of Example 1 using the lytic reagent composition of formula 1 a containing tetrazole as the hemoglobin ligand, and COULTER® ISOTON® II (a commercial blood diluent) as the diluent. FIG. 2 illustrates a total of twelve spectra acquired from 12 seconds to 12 hours after the addition of the lytic reagent composition with an interval of one hour. The spectra of the Hgb-tetrazole chromogen are very stable and exhibit no shift or decay during twelve hours data collection time.

The nature of a specific hemoglobin chromogen depends on the organic ligand used in the lytic reagent composition. Most chromogens formed by treating the blood sample with the lytic reagent composition of the present invention using the organic ligands described above have their maximum absorptions between about 510 nm and about 560 nm. Therefore, the chromogens can be measured by most commercial blood analyzers with incorporation of the absorption coefficient of the specific chromogen.

Figure 3A:
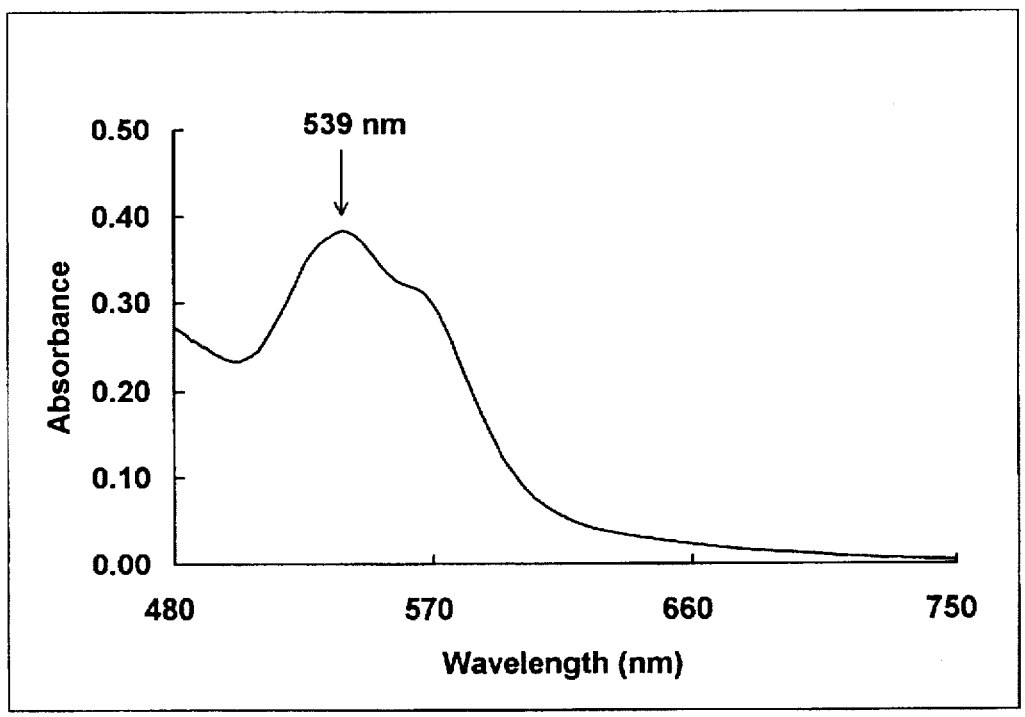
FIGS. 3a and 3b show the spectra of a whole blood sample treated according to the procedure described in Example 2, using the lytic reagent composition of Example 2, and standard phosphate buffered saline and a commercial blood diluent, COULTER® ISOTON® III as diluents.
Figure 3B:
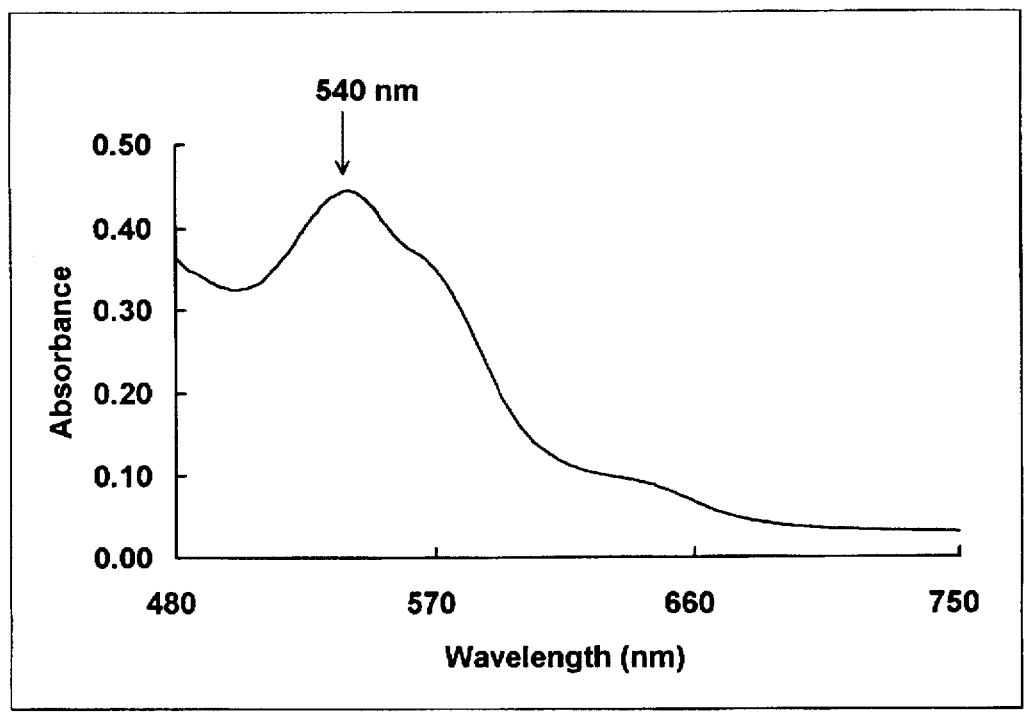

The lytic reagent composition of the present invention can be used with many suitable blood diluent. FIG. 3 shows the spectra of a whole blood sample treated by the procedure described above using the lytic reagent composition containing tetrazole (Example 2), and using standard phosphate buffered saline and a commercial blood diluent, COULTER® ISOTON® III, as the diluents. With both diluents, basically the same hemoglobin chromogen forms, which can be measured at 540 nm.

Figure 4A:
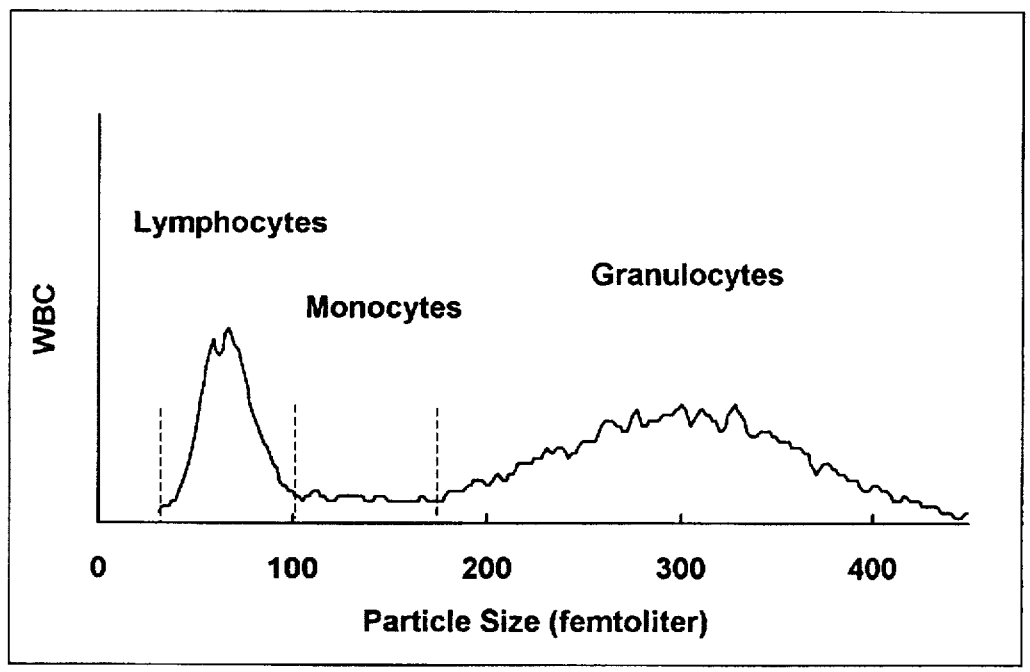
FIGS. 4a, 4b, 4c and 4d show the leukocyte subpopulation distribution histograms of four whole blood samples obtained by using the lytic reagent compositions of Example 4 of the present invention on a commercial blood analyzer, COULTER COUNTER® Model S-Plus IV.
Figure 4B:
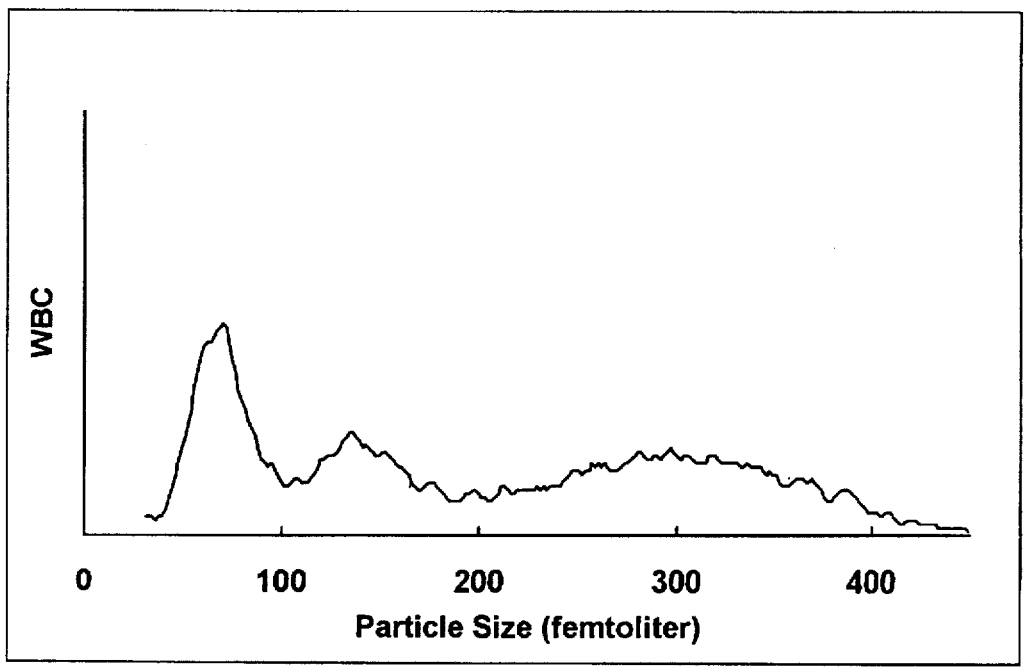
Figure 4C:
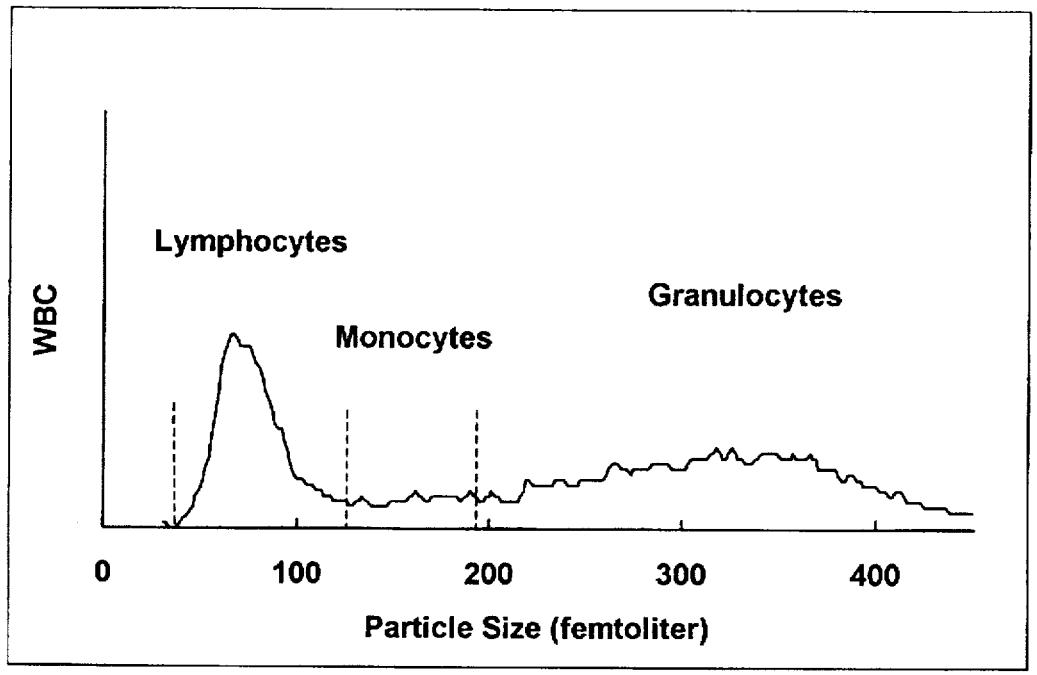
Figure 4D:
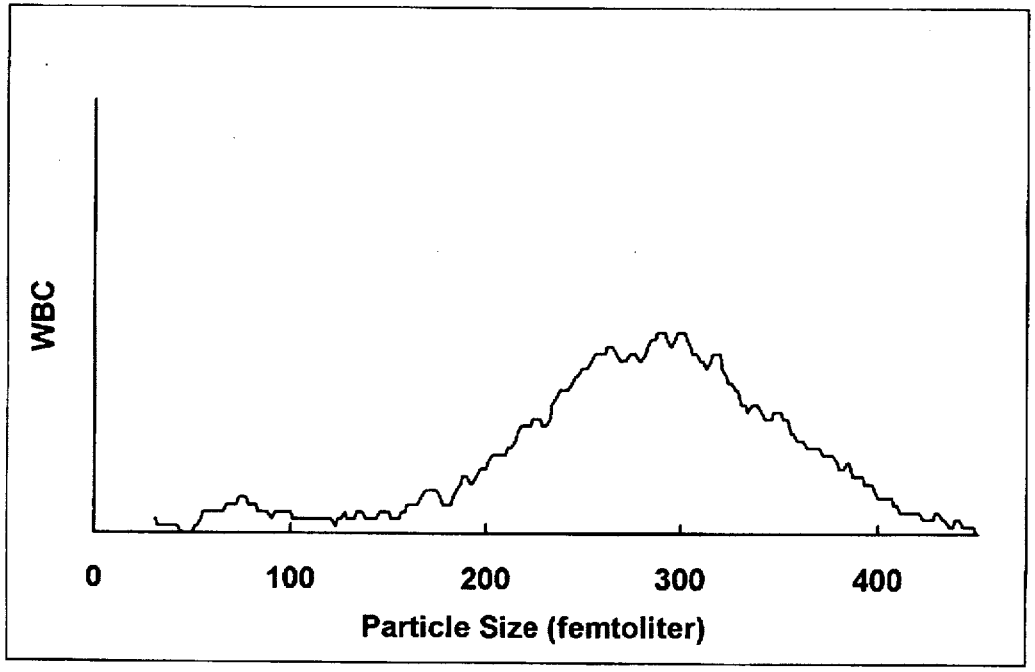
Figure 6B:
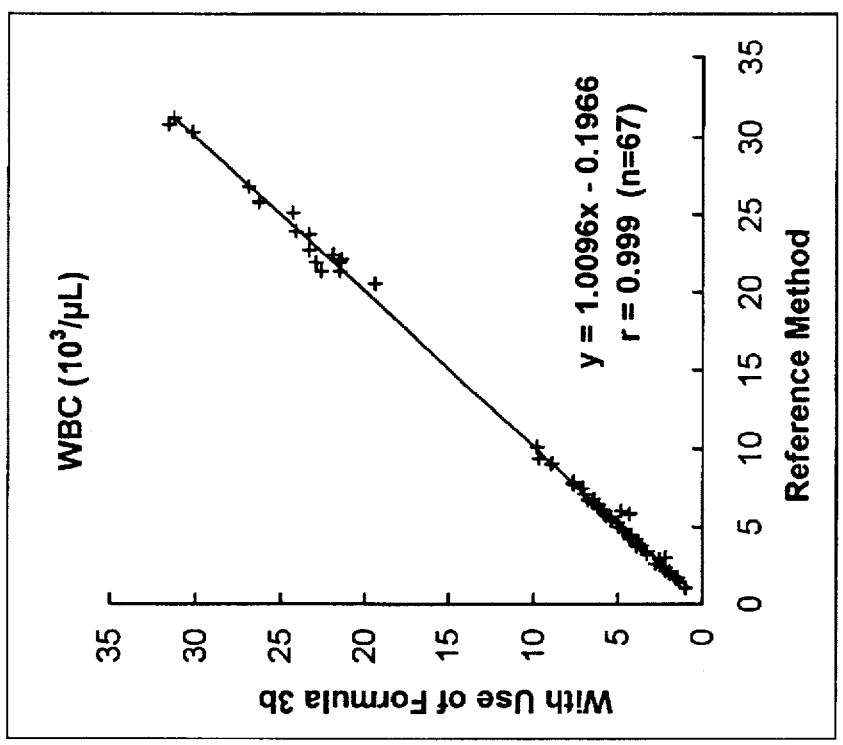
FIGS. 6a and 6b show the correlations between the hemoglobin concentration and the numbers of leukocytes obtained on an automated commercial blood analyzer, COULTER® STKS using COULTER® LYSE S® III diff lytic reagent and the results obtained using a lytic reagent composition of Example 3 (formula 3b) of the present invention on the same instrument.

Unlike the previous reagents, the lytic reagent composition of the present invention has a broad pH range, from 1 to 13. This broadens the scope of chemicals which can be used as a hemoglobin ligand. For instance, potassium salt of oxonic acid forms a stable chromogen with hemoglobin which has a strong absorption at 538 nm. However, potassium salt of oxonic acid is only readily soluble in water at low pH, less than pH 3. The previous neutral and alkaline reagents exclude using this chemical for hemoglobin measurement. Sakata teaches in U.S. Pat. No. 5,242,832 that If the pH value is 3.0 or less, damage to the leukocytes increases thus rendering measurement of the leukocytes difficult. FIG. 4 shows leukocyte subpopulation distribution histograms obtained following the procedure of the present invention using a lytic reagent composition of Example 4, which contains 0.5% of potassium salt of oxonic acid and has a pH of 2.3, and COULTER® ISOTON® III as the diluent. As illustrated by FIG. 4c and 4d, the leukocytes are clearly differentiated into lymphocytes, monocytes and granulocytes. FIG. 6b shows an excellent linear correlation between the numbers of leukocytes obtained on a commercial automated blood analyzer, COULTER® STKS, and the results obtained using one of the lytic reagent compositions of the Example 3 (formula 3b) on the same instrument, wherein pH of the lytic reagent composition is only 1.67.

Figure 5B:
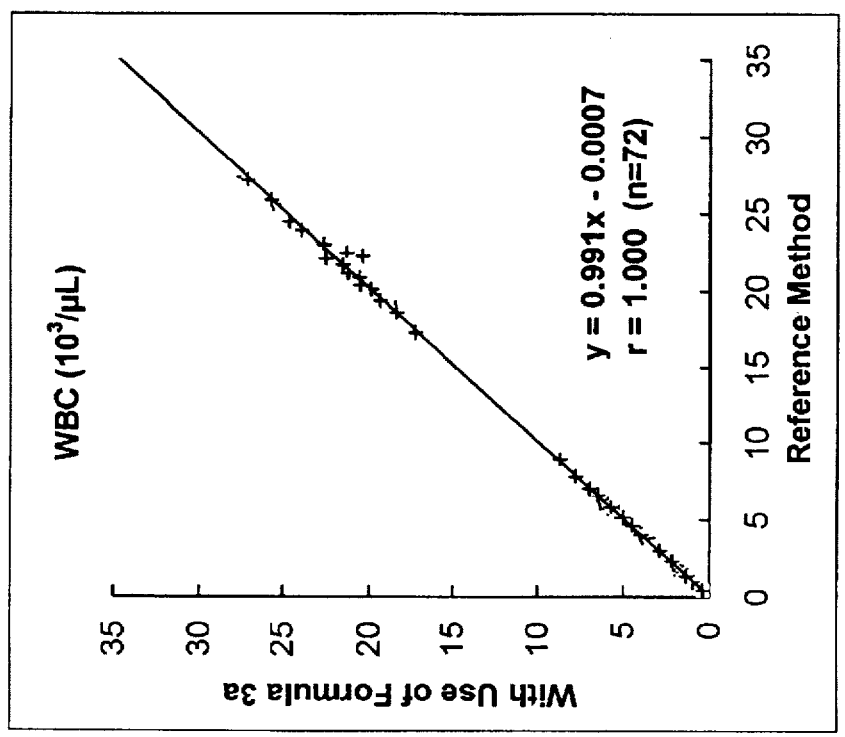
FIGS. 5a and 5b show the correlations between the hemoglobin concentration and the numbers of leukocytes obtained on an automated commercial blood analyzer, COULTER® STKS using a conventional lytic reagent, COULTER® LYSE S® III diff, and the results obtained using a lytic reagent composition of Example 3 (formula 3a) of the present invention on the same instrument.
Figure 5A:
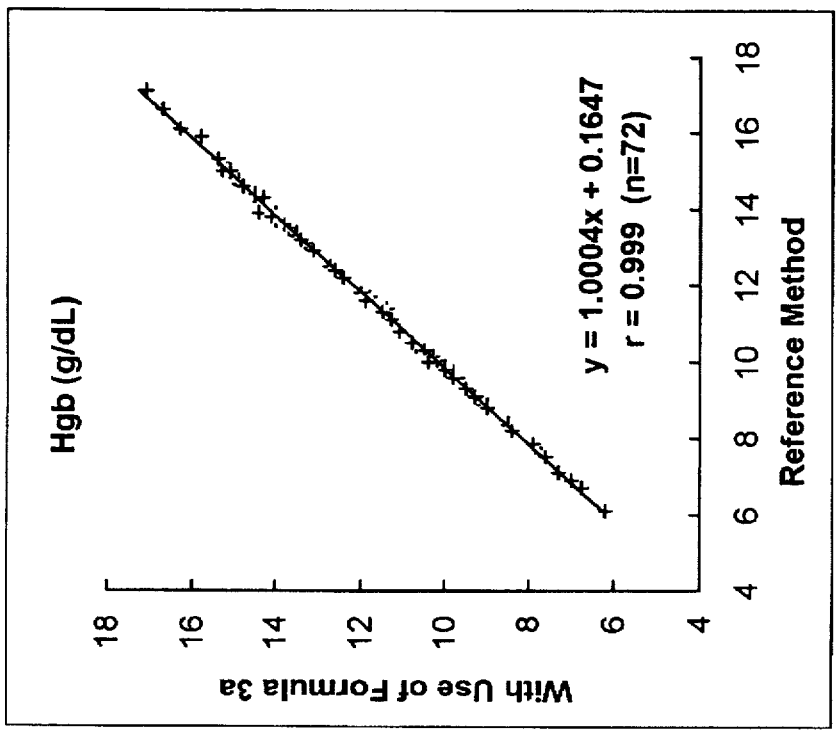
Figure 6A:
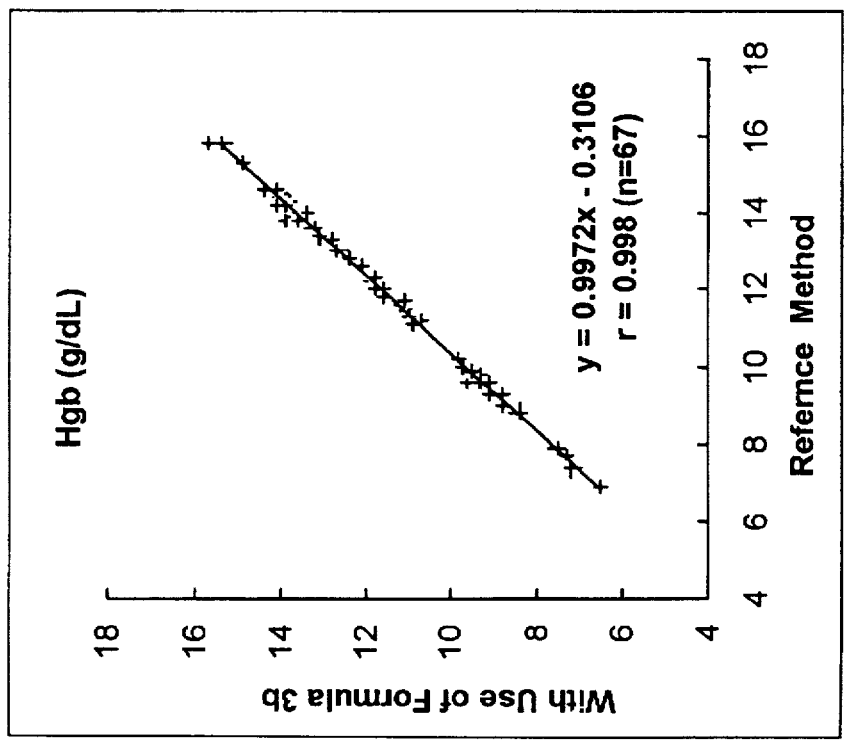
Figure 7B:
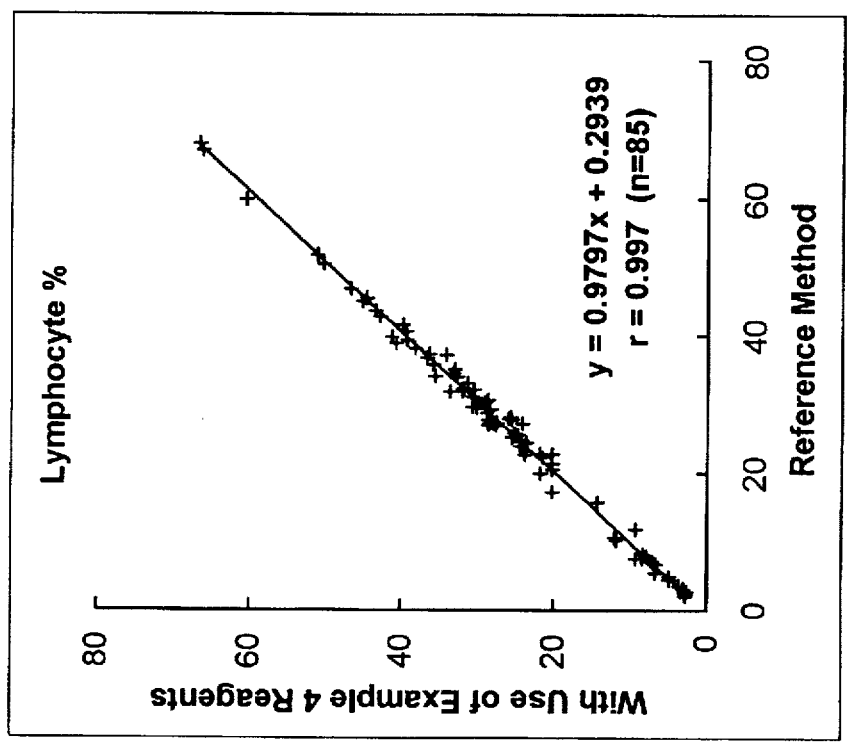
FIGS. 7a, 7b, 7c, 7d and 7e show the correlations between the numbers of leukocytes, the leukocyte differential count and hemoglobin concentration obtained on a COULTER COUNTER® Model S-Plus IV and the results obtained using a lytic reagent composition (formula 4a and the diluent) of Example 4 of the present invention on the same commercial instrument.
Figure 7A:
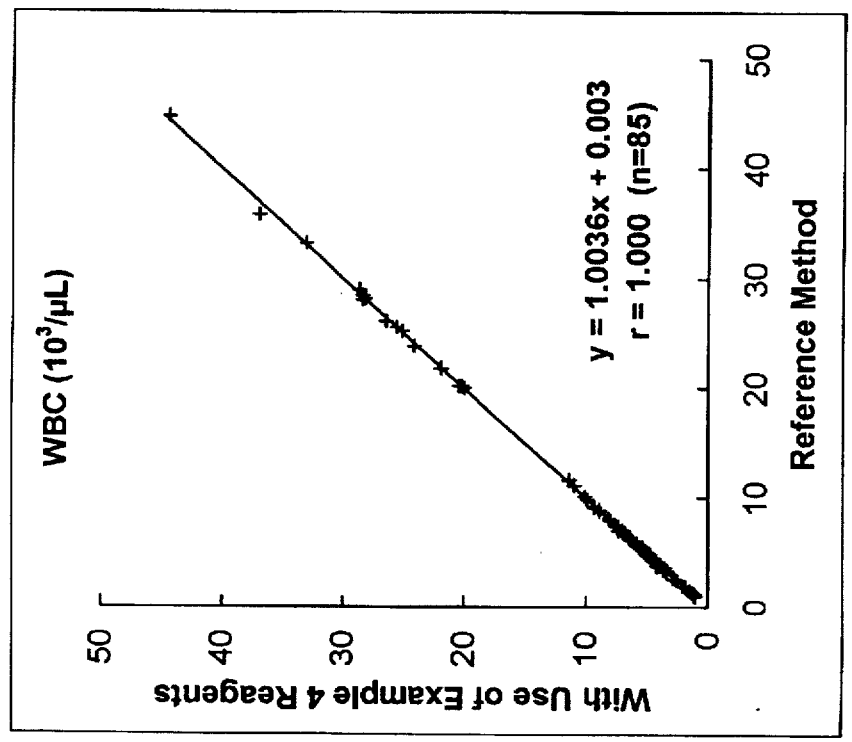
Figure 7D:
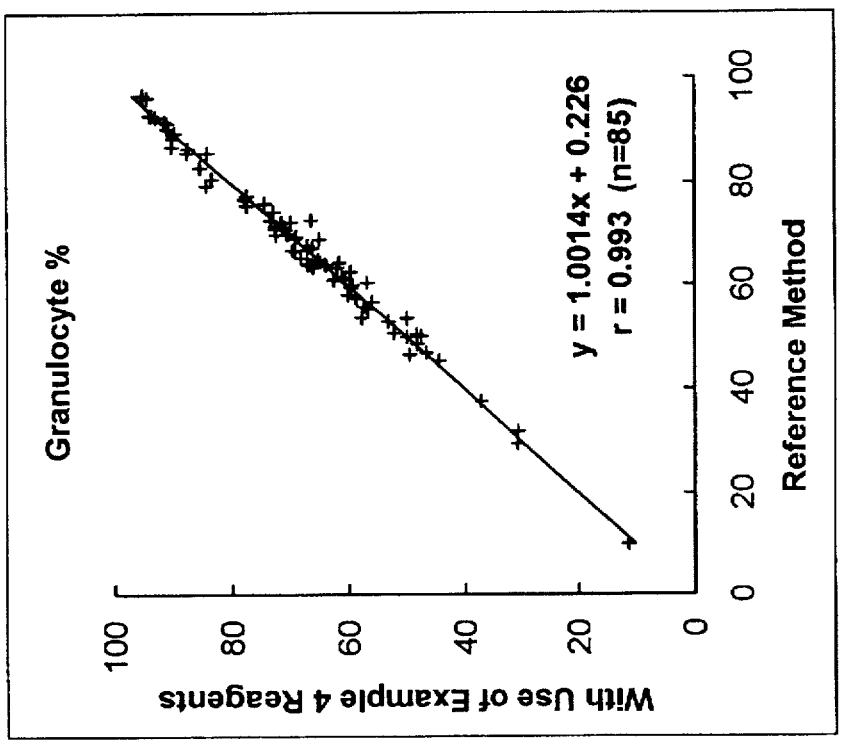
Figure 7C:
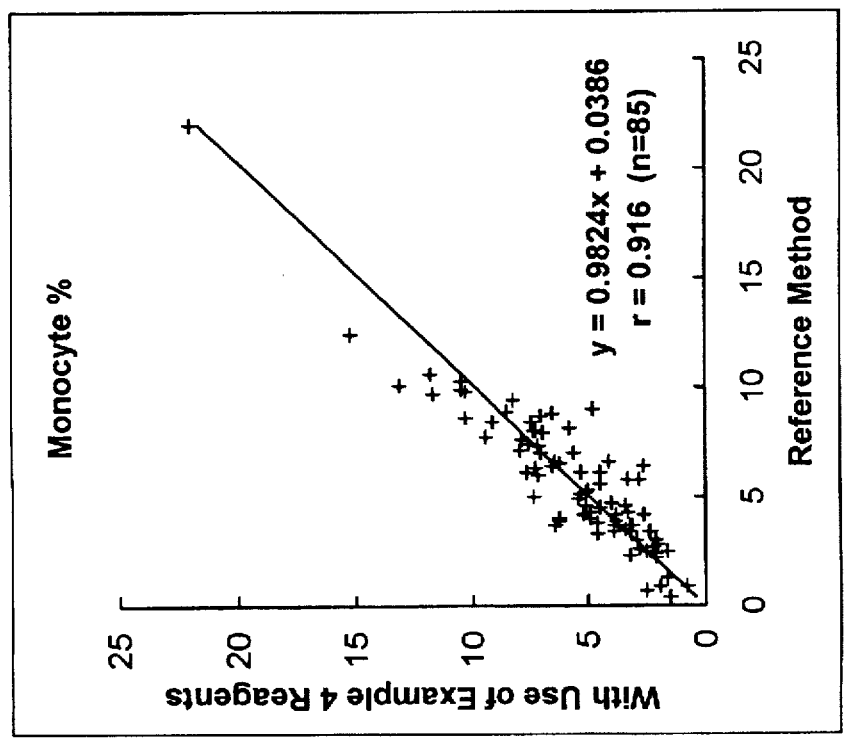
Figure 7E:
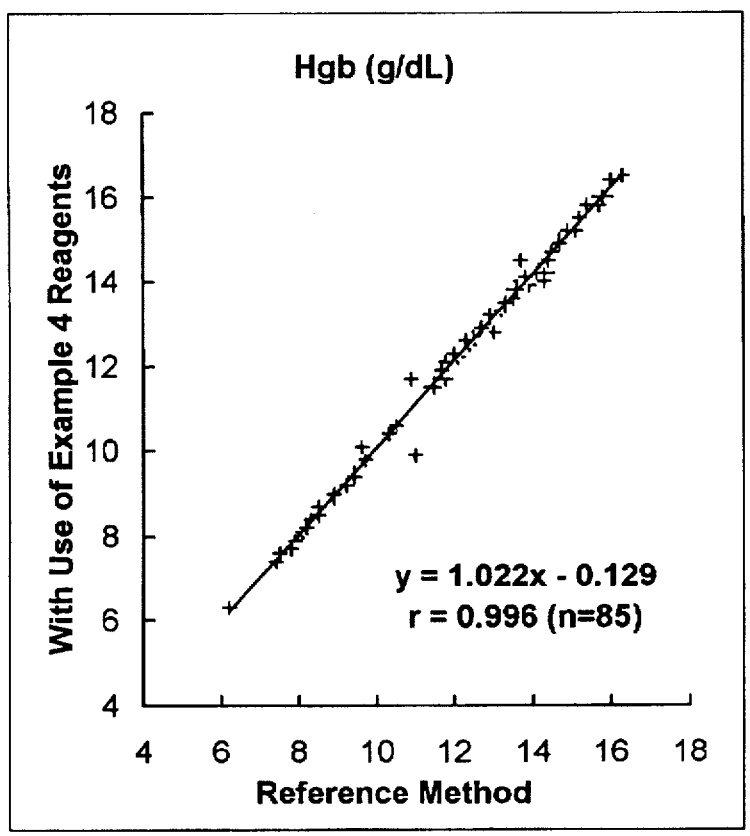

The lytic reagent composition of the present invention and the method of using the same provide an accurate hemoglobin measurement, accurate count of leukocytes and differential counting of leukocyte subpopulations. FIG. 5a and 6a demonstrate an excellent linear correlation between the hemoglobin concentrations obtained on a COULTER® STKS using a conventional lytic reagent and the hemoglobin concentrations obtained using the lytic reagent compositions of Example 3 (formula 3a and 3b). FIG. 5b and 6b illustrate excellent correlation between the leukocyte count obtained on a COULTER® STKS, and the results obtained using formula 3a and 3b on the same instrument.

The lytic reagent composition of the present invention provides an accurate hemoglobin measurement in the presence of common interference materials. Totally 72 whole blood samples were analyzed using the formula 3a of Example 3 on a COULTER® STKS. 70% of the samples are clinical samples including various diseases such as sickle cell crisis and hepatitis C. It is known that these abnormal bloods contain abnormal hemoglobins and interference materials for hemoglobin measurement. However, the results of measurement using the lytic reagent composition and the method of the present invention correlate excellently with the conventional cyanide-Hgb method, as illustrated by FIGS. 5 and 6, demonstrating that the total hemoglobin concentration of various clinical samples can be measured by using the lytic reagent composition of the present invention.

Figure 9A:
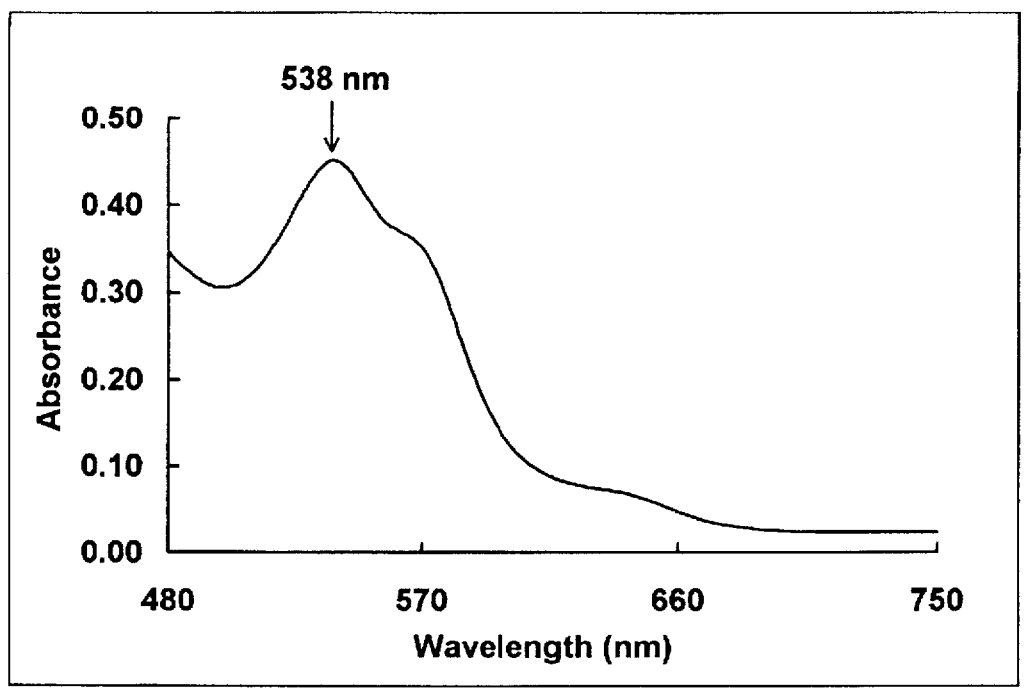
FIGS. 9a and 9b show a spectra and a leukocyte subpopulation distribution histogram of a whole blood sample treated according to the procedure described in Example 6, using a lytic reagent and a diluent composition of Example 6.
Figure 9B:
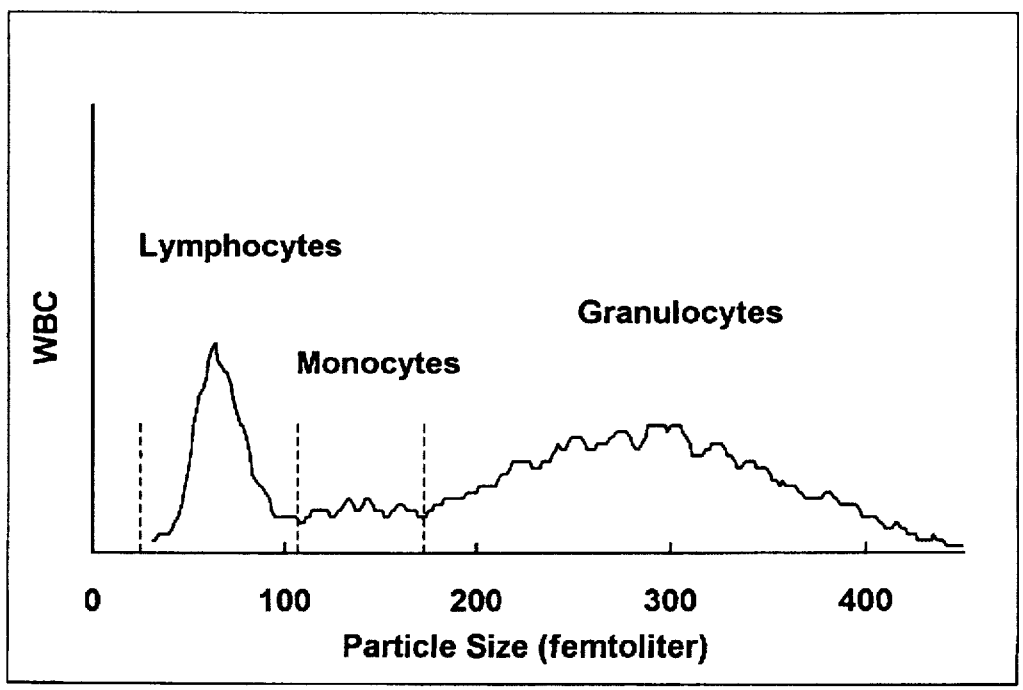

Another mode of utilizing the hemoglobin stabilization functionality of the organic ligands is to add the organic ligand into a blood diluent instead of the lytic reagent composition. According the method described above, a blood sample is prediluted by the blood diluent before mixed with the lytic reagent. When a diluent contains an organic ligand described above, the hemoglobin molecules in the sample mixture after released from the erythrocytes by a lytic reagent will be in immediate contact with the organic ligand to form a stable hemoglobin chromogen. Therefore, the alternative mode serves the same purpose for hemoglobin measurement of a blood sample. However, it provides options to reagent designers to choose the most appropriate mode based on their specific need, for instance, the compatibility of an organic ligand to other tests that the lytic reagent or the diluent are required to perform beside the hemoglobin measurement, or an organic ligand's compatibility to other chemical ingredients in either lytic reagent or the diluent. Example 5 illustrates such an application of the organic ligands in blood diluent to form stable hemoglobin chromogens, wherein the lytic reagent contains only the hemolytic surfactant. FIG. 9a shows a spectra of a blood sample treated according to the procedure of Example 6 using a diluent containing triazole as the hemoglobin ligand. The characteristics of the chromogen is the same to the one obtained using a lytic reagent composition containing the same ligand as shown in FIG. 1a. FIG. 9b shows a leukocyte distribution histogram of a blood sample obtained by using the diluent of Example 6 on a COULTER COUNTER® Model S-Plus IV, wherein the lytic reagent contains only surfactant. This example shows the compatibility of the organic ligand to the leukocyte differential analysis when it is used in the alternative mode.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

The reagents of the following compositions were prepared.

| Formula 1a | |
|---|---|
| tetrazole | 5.0 g |
| tetradecyltrimethylammonium bromide | 15.0 g |
| distilled water adjusted to 1 liter | |
| pH | 2.77 |
| Formula 1b | |
| triazole | 10.0 g |
| dodecyltrimethylammmonium chloride (50% solution) | 35.0 ml |
| tetradecyltrimethylammmonium bromide | 3.5 g |
| distilled water adjusted to 1 liter | |
| pH | 6.19 |
| Formula 1c | |
| quinaldic acid | 5.0 g |
| dodecyltrimethylammonium chloride (50% solution) | 50.0 ml |
| distilled water adjusted to 1 liter | |
| pH | 2.55 |
| Formula 1d | |
| melamine | 5.0 g |
| tetradecyltrimethylammmonium bromide | 3.6 g |
| dodecyltrimethylammonium chloride (50% solution) | 36.0 ml |
| distilled water adjusted to 1 liter | |
| pH | 4.55 |
| Formula 1e | |
| tetrazole | 5.0 g |
| Chemfac NB-104 | 30.0 g |
| (complex phosphate ester made by Chemax, Inc.) | |
| distilled water adjusted to 1 liter | |
| pH | 7.11 |

Figure 1B:
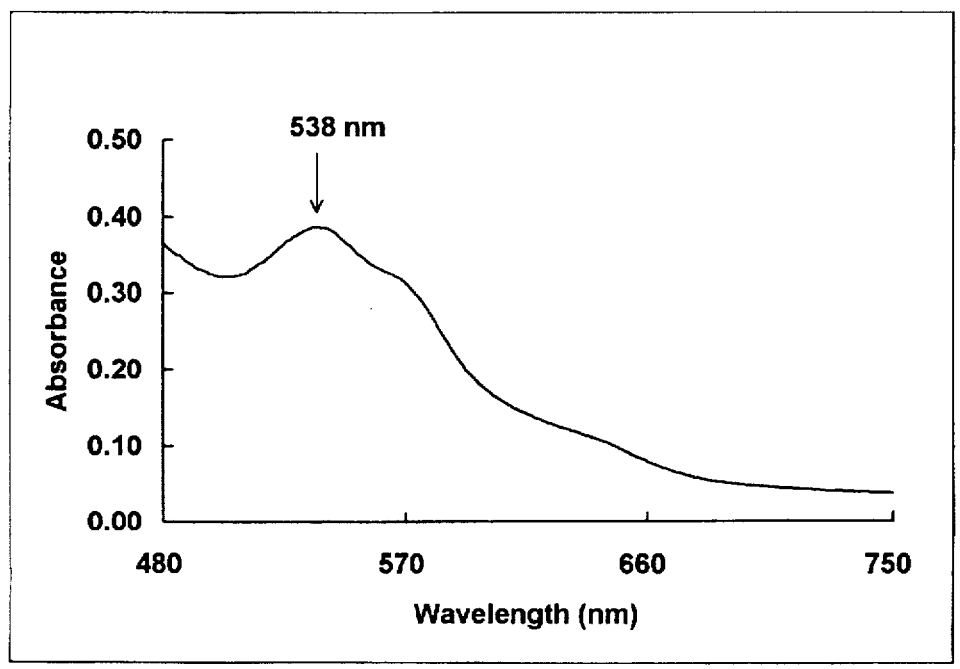

11.6 µl of a whole blood sample was diluted by 2500 µl of ISOTON® II, then 403 µl one of the above lytic reagent compositions was mixed manually with the prediluted sample. The absorption spectrum of the sample was measured immediately on a Beckman DU 7500 spectrophotometer. FIG. 1a to 1b show the spectra of the blood samples treated according to above procedure using formula 1b and 1c. FIG. 2 shows a total of twelve spectra obtained from a blood sample processed according to above procedure using formula 1a. The spectra were acquired from 12 seconds to 12 hours after the addition of the lytic reagent composition with an interval of one hour.

EXAMPLE 2

A reagent of the following composition was prepared.

| | |
|---|---|
| tetrazole | 5.0 g |
| dodecyltrimethylammonium chloride (50% solution) | 36.0 ml |
| tetradecylammnonium bromide | 3.6 g |
| distilled water | 1 liter |
| pH | 2.73 |

11.6 µl of a whole blood sample was diluted by 2500 µl of a blood diluent, then 403 µl of the above formula was mixed manually with the prediluted sample. The absorption spectrum of the sample was measured immediately on a Beckman DU 7500 spectrophotometer. Five commercial blood diluents were used for the hemoglobin measurement, i.e., COULTER® ISOTON® III, COULTER® ISOTON® II, Technicon H*™ Systems RBC DIL (a commercial product of Technicon Instruments Corp.), the standard phosphate buffered saline and the standard sodium chloride saline. The chromogen formed has a maximum absorption peak at about 540 nm with a shoulder at about 565 nm. The maximum absorption of the chromogen is only slightly different when different diluents used for the hemoglobin measurement, i.e., 540 nm with the ISOTON® III, 539 nm with the ISOTON® II, the Technicon H*™ Systems RBC DIL, and the standard phosphate buffered saline and 538 nm with the standard sodium chloride saline. The chromogen formed immediately after addition of the above lytic reagent compositions, from 8 seconds to about 35 seconds depending on the blood diluent used. FIG. 3 shows the spectra obtained following above procedure, using the standard phosphate buffered saline and ISOTON® III as the diluents.

EXAMPLE 3

The reagents of the following compositions were prepared.

| Formula 3a | |
|---|---|
| tetrazole | 5.0 g |
| tetradecyltrimethylammonium bromide | 15.0 g |
| distilled water adjusted to 1 liter | |
| pH | 12.06 |
| Formula 3b | |
| aniline-2-sulfonic acid | 5.0 g |
| tetradecyltrimethylammnonium bromide | 10.0 g |
| cetyltrimethylammonium bromide | 4.0 g |
| distilled water | 1 liter |
| pH | 1.67 |
| Formula 3c | |
| quinaldic acid | 5.0 g |
| dodecyltrimethylammonium chloride (50% solution) | 40.0 ml |
| distilled water | 1 liter |
| pH | 2.58 |

About 70 blood samples, whose hemoglobin concentration ranged from 6 to 17 g/dL and leukocyte count ranged from 1,000 µL to 40,000/µL, were analyzed on a calibrated COULTER® STKS instrument under standard instrument configuration except the lytic reagent, the LYSE S® III diff being replaced by the above formulations. For each formula, about half of the samples are clinical samples including various diseases. In the case of formula 3a, 70% of samples are clinical samples. FIG. 5 shows the correlations between the hemoglobin concentration and the numbers of leukocytes (reported as WBC in $10^3$/µL) obtained by using the reference reagent, LYSE S® III diff, and the results obtained using the formula 3a on the same instrument. FIG. 6 shows the correlations between the hemoglobin concentration and the numbers of leukocytes obtained by using the LYSE S® III diff lytic reagent and the results obtained using the formula 3b on the same instrument.

FIGS. 5 and 6 demonstrate excellent linear correlations between the lytic reagent compositions of the present invention and the conventional cyanide-containing lysing reagent in hemoglobin concentration and WBC measurements.

EXAMPLE 4

The reagents of the following compositions were prepared.

| Lytic reagent | |
|---|---|
| Formula 4a | |
| triazole | 10.0 g |
| dodecyltrimethylammonium chloride (50% solution) | 35.0 ml |
| tetradecyltrimethylammnonium bromide | 3.5 g |
| distilled water adjusted to 1 liter | |
| pH | 6.39 |
| Formula 4b | |
| oxonic acid potassium salt | 5.0 g |
| dodecyltrimethylammonium chloride (50% solution) | 35.0 ml |
| tetradecyltrimethylammnonium bromide | 3.5 g |
| distilled water adjusted to 1 liter | |
| pH was adjusted to 2.3 by HCl | |
| Diluent | |
| sodium sulfate | 9.7 g |
| sodium chloride | 4.0 g |
| distilled water adjusted to 1 liter | |
| pH adjusted to 7.14 by 1% NaOH | |

82 blood samples, whose hemoglobin concentration ranged from 6 to about 17 g/dL and leukocyte count ranged from 1,500/µL to 45,000/µL, were analyzed on a calibrated COULTER COUNTER® Model S-Plus IV under standard instrument configuration using reference reagents, LYSE S® III diff and ISOTON® III. Then the same samples were analyzed again on the same instrument except that the lytic reagent, the LYSE S® III diff, was replaced by the above lytic reagent compositions and the ISOTON® III was replaced by the above diluent. FIG. 4 shows the leukocyte subpopulation distribution histograms from four of these blood samples obtained on the COULTER COUNTER® Model S-Plus IV. FIGS. 4a and 4b were obtained using Formula 4a and the above diluent, wherein FIG. 4a showing a histogram of a normal blood and FIG. 4b showing a histogram of a blood sample having elevated monocytes. FIGS. 4c and 4d were obtained using Formula 4b and ISOTON® III, wherein FIG. 4c showing a histogram of a normal blood and FIG. 4d showing a histogram of a clinical sample having more than 90% of granulocytes. FIGS. 7a to 7e show the correlations between the numbers of leukocytes (reported as WBC in $10^3$/µL, FIG. 7a), lymphocyte % (FIG. 7b), monocyte% (FIG. 7c), granulocyte % (FIG. 7d) and hemoglobin concentration (FIG. 7e) obtained by using the reference reagents and those obtained using Formula 4a and the above diluent. The correlation coefficients, as well as the slopes and the intercepts of the regression lines demonstrate excellent linear correlations for hemoglobin concentration, WBC, lymphocyte % and granulocyte %, and a good correlation for monocyte %.

EXAMPLE 5

| Lytic reagent | |
|---|---|
| dodecyltrimethylammonium chloride (50% solution) | 36.0 ml |
| tetradecyltrimethylammmonium bromide | 3.6 g |
| distilled water adjusted to 1 liter | |
| pH | 6.88 |
| Diluent | |
| Formula 5a | |
| tetrazole | 5 g |
| standard phosphate buffered saline | 1 liter |
| pH | 3.86 |
| Formula 5b | |
| 2-amino-1,3,4-thiazole | 5.0 g |
| sodium sulfate | 9.7 g |
| sodium chloride | 4.0 g |
| distilled water adjusted to 1 liter | |
| pH | 6.04 |

Figure 8A:
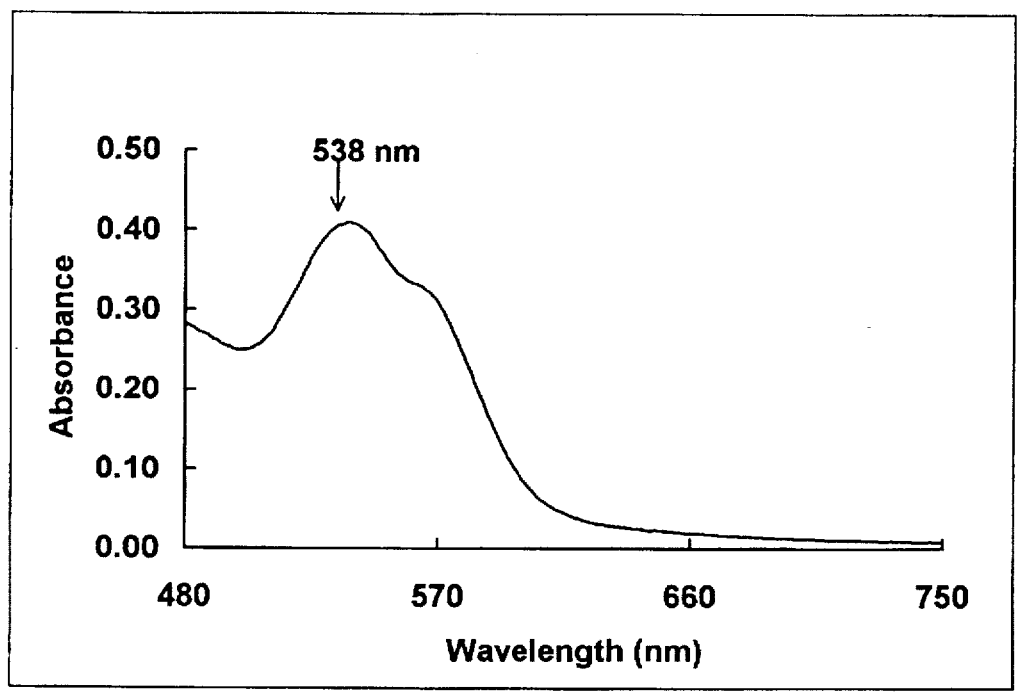
FIGS. 8a and 8b are the absorption spectra of two whole blood samples processed according to the procedure described in Example 5 using a lytic reagent and the diluent compositions of Example 5 of the present invention (formula 5a and 5b).
Figure 8B:
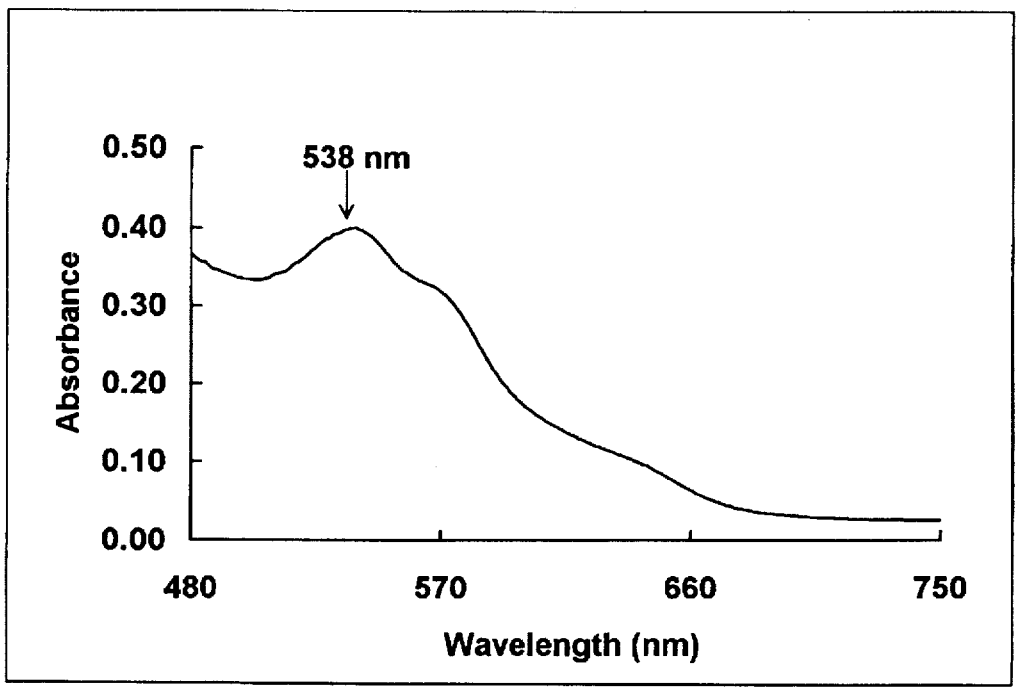

11.6 µl of a whole blood sample was diluted by 2500 µl one of the above diluent formula, then 403 µl of above lytic reagent formula was mixed manually with the prediluted sample. The absorption spectrum of the sample was measured immediately on a Beckman DU 7500 spectrophotometer. FIGS. 8a to 8b show the spectra of the blood samples treated according to above procedure using formula 5a and 5b, respectively.

EXAMPLE 6

| Lytic reagent | |
|---|---|
| dodecyltrimethylammonium chloride (50% solution) | 36.0 ml |
| tetradecyltrimethylammmonium bromide | 3.6 g |
| distilled water adjusted to 1 liter | |
| pH | 6.88 |
| Diluent | |
| triazole | 5.0 g |
| sodium sulfate | 9.7 g |
| sodium chloride | 4.0 g |
| distilled water adjusted to 1 liter | |
| pH | 6.06 |

10 blood samples were analyzed on a calibrated COULTER COUNTER® Model S-Plus IV using the above lytic reagent and diluent. FIG. 9a shows a leukocyte subpopulation distribution histogram of a blood sample obtained on the COULTER COUNTER® Model S-Plus IV. These samples were also treated and measured on the spectrometer according the procedure described in Experiment 5 using the above lytic reagent and diluent. FIG. 9a shows a spectrum of the same blood sample used in FIG. 9b. Both spectrum and the leukocyte subpopulation distribution histogram have the same characteristics to those obtained when triazole is used in the lytic reagent composition.

What is claimed is:

1. A cyanide-free lytic reagent composition comprising an aqueous solution of:

(I) at least one surfactant in a sufficient amount to hemolyse erythrocytes and release hemoglobin for a determination of hemoglobin concentration selected from the group consisting of:

(a) quaternary ammonium salts, represented by the following molecular structure:

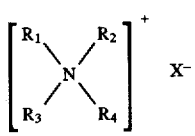

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions;

(b) pyridinium salts represented by the following molecular structure:

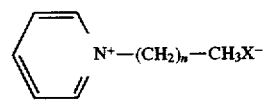

wherein n is an integer from 7 to 12 and $X^-$ is an anionic group;

(c) alkyl sulfonic acid, or alkaline metal salts of alkyl sulfonates; and (d) organic phosphate esters, or alkaline metal salts of organic phosphate ester; and (II) an organic ligand in a sufficient amount to form a stable chromogen with hemoglobin selected from the group consisting of:

(a) triazole and its derivatives (b) tetrazole and its derivatives (c) alkaline metal salts of oxonic acid having the following Formula:

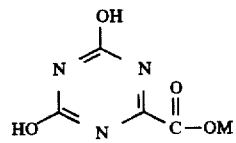

wherein M is an alkaline metal cation;

(d) melamine

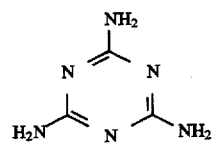

(e) aniline-2-sulfonic acid

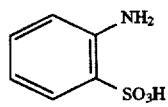

(f) quinaldic acid

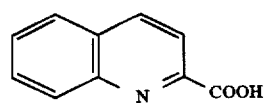

(g) 2-amino-1,3,4-thiadiazole

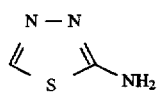

(h) triazine and its derivatives having the following Formula:

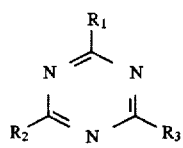

wherein $R_1$, $R_2$ and $R_3$ are —H, —OH, —SH, —COOH and heterocyclic derivatives of triazine;

(I) urazole

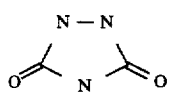

(j) DL-pipecolinic acid

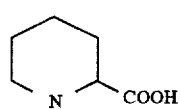

(k) isonicotinamide

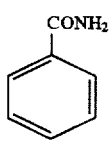

(l) anthranilonitrile

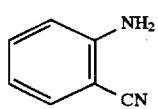

(m) 6-aza-2-thiothymine

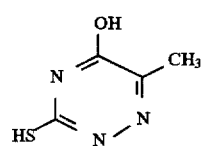

(n) adenine

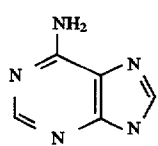

3-(2-thienyl)acrylic acid

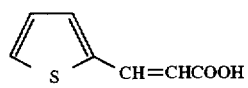

(p) benzoic acid, or alkali metal and ammonium salts of benzoic acid having the following Formula:

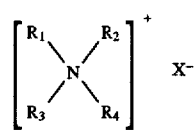

wherein R is —H, $NH_4^+$ or and alkali metal cations; and (q) pyrazine and its derivatives having the following Formula:

$$\begin{array}{c} R_3 \diagdown \; N \; \diagup R_1 \\ R_4 \diagup \; N \; \diagdown R_2 \end{array}$$

wherein $R_1$, $R_2$ $R_3$ and $R_4$ are —H, —CN, —OH, —SH, —COOH, or —CONH$_2$; and whereby a pH of the lytic reagent composition ranges from 1 to 13.

2. The lytic reagent composition of claim 1, wherein the at least one surfactant comprises a quaternary ammonium salt having a concentration ranging from about 2 g/L to about 250 g/L.

3. The lytic reagent composition of claim 1, wherein the at least one surfactant comprises a pyridinium salt having a concentration ranging from about 2 g/L to about 130 g/L.

4. The lytic reagent composition of claim 1, wherein the at least one surfactant comprises an alkyl sulfonic acid, or alkaline metal salt of an alkyl sulfonate having a concentration ranging from about 8 g/L to about 30 g/L.

5. The lytic reagent composition of claim 1, wherein the at least one surfactant comprises an organic phosphate ester, or alkaline metal salt of an organic phosphate ester having a concentration ranging from about 15 g/L to about 70 g/L.

6. The lytic reagent composition of claim 1, wherein the organic ligand has concentrations in a range of about 1 g/L to about 30 g/L.

7. The cyanide-free lytic reagent composition of claim 1, wherein the at least one surfactant is selected from the group consisting of:

(a) quaternary ammonium salts, represented by following molecular structure:

$$\begin{bmatrix} R_1 \diagdown \;\; \diagup R_2 \\ N \\ R_3 \diagup \;\; \diagdown R_4 \end{bmatrix}^+ X^-$$

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions; and (b) pyridinium salts represented by following molecular structure:

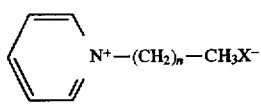

wherein n is an integer from 7 to 12 and $X^-$ is an anionic group; and whereby said at least one surfactant is in a sufficient amount to hemolyse erythrocytes and release hemoglobin for a determination of hemoglobin concentration and preserve nuclei of leukocytes for a determination of leukocyte count.

8. The lytic reagent composition of claim 7, wherein the at least one surfactant comprises a quaternary ammonium salt having a concentration ranging from about 4 g/L to about 150 g/L.

9. The lytic reagent composition of claim 7, wherein the at least one surfactant comprises a pyridinium salt having a concentration ranging from about 2 g/L to about 130 g/L.

10. The lytic reagent composition of claim 7, wherein the organic ligand has concentrations in a range of about 1 g/L to about 30 g/L.

11. The cyanide-free lytic reagent composition of claim 7, wherein:

(I) the at least one surfactant is a quaternary ammonium salt, represented by following molecular structure:

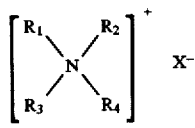

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions; whereby said at least one surfactant is in a sufficient amount to hemolyse erythrocytes and release hemoglobin for a determination of hemoglobin concentration and preserve nuclei of leukocyte subpopulations for a differential analysis of leukocytes; and wherein (II) the organic ligand in a sufficient amount to form a stable chromogen with hemoglobin is selected from the group consisting of:
  (a) triazole and its derivatives
  (b) melamine

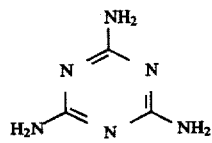

(c) alkaline metal salts of oxonic acid having the following Formula:

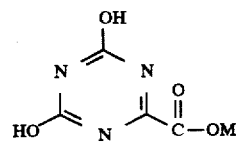

wherein M is an alkaline metal cation;

(d) 2-amino-1,3,4-thiadiazole

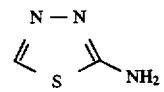

(e) triazine and its derivatives having the following Formula:

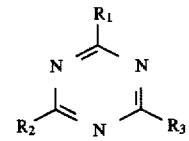

wherein $R_1$, $R_2$ and $R_3$ are —H, —OH, —SH, —COOH and heteracyclic derivatives of triazine;
(f) urazole

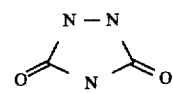

(g) DL-pipecolinic acid

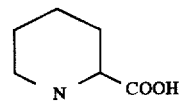

(h) isonicotinamide; and

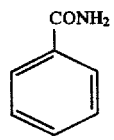

(i) pyrazine and its derivatives having the following Formula:

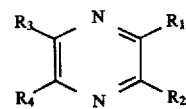

wherein $R_1$, $R_2$ $R_3$ and $R_4$ are —H, —CN, —OH, —SH, —COOH or —CONH$_2$; and whereby the pH of the lytic reagent composition ranges from 2 to 10.

12. The lytic reagent composition of claim 11 wherein the quaternary ammonium salt has a concentration ranging from about 4 g/L to about 50 g/L.

13. The lytic reagent composition of claim 11 wherein the organic ligand has concentrations in a range of about 1 g/L to about 30 g/L.

14. A method of measuring total hemoglobin concentration of a blood sample using the cyanide-free lytic reagent composition of claim 1 comprising:

(a) diluting a blood sample with a blood diluent;
(b) mixing the diluted blood sample with the cyanide-free lytic reagent composition of claim 1 to lyse erythrocytes and to form a stable hemoglobin chromogen;
(c) measuring absorbance of the formed hemoglobin chromogen at a predetermined wavelength;

(d) determining total hemoglobin concentration of said blood sample from the measured absorbance of the hemoglobin chromogen; and (e) reporting the total hemoglobin concentration of said blood sample.

15. The method of claim 14, wherein the absorbance of said blood sample is measured between about 510 nm and about 560 nm.

16. The method of claim 14, wherein the at least one surfactant in the lytic reagent composition is selected from the group consisting of:

(a) quaternary ammonium salts, represented by following molecular structure:

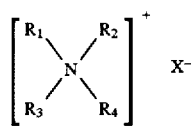

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions; and (b) pyridinium salts represented by following molecular structure:

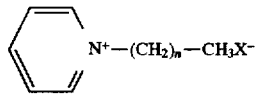

wherein n is an integer from 7 to 12 and $X^-$ is an anionic group; and whereby said at least one surfactant is in a sufficient amount to hemolyse erythrocytes and release hemoglobin for a determination of hemoglobin concentration and preserve nuclei of leukocytes for a determination of leukocyte count; and further comprising the steps of:

counting the number of leukocytes in said blood sample on an automated blood analyzer utilizing DC impedance measurement; and reporting the number of leukocytes for said blood sample.

17. The method of claim 14, wherein:

(I) the at least one surfactant is a quaternary ammonium salt, represented by following molecular structure:

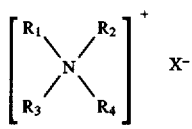

wherein $R_1$ is an alkyl alkenyl or alkynyl group having 10 to 18 carbon atoms; $R_2$, $R_3$ and $R_4$ are alkyl groups having 1 to 4 carbon atoms and $X^-$ is chloride or bromide anions; whereby said at least one surfactant is in a sufficient amount to hemolyse erythrocytes and release hemoglobin for a determination of hemoglobin concentration and preserve nuclei of leukocyte subpopulations for a differential analysis of leukocytes; and wherein (II) the organic ligand in a sufficient amount to form a stable chromogen with hemoglobin is selected from the group consisting of:

(a) triazole and its derivatives (b) melamine

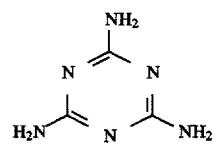

(c) alkaline metal salts of oxonic acid having the following Formula:

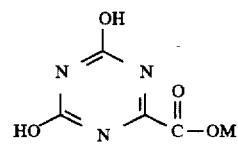

wherein M is an alkaline metal cation;

(d) 2-amino-1,3,4-thiadiazole

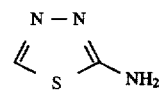

(e) triazine and its derivatives having the following Formula:

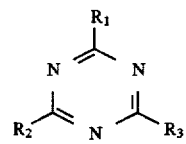

wherein $R_1$, $R_2$ and $R_3$ are —H, —OH, —SH, —COOH and heteracyclic derivatives of triazine;

(f) urazole

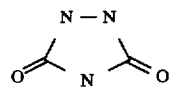

(g) DL-pipecolinic acid

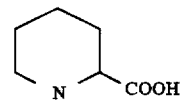

(h) isonicotinamide; and

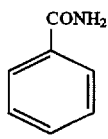

(i) pyrazine and its derivatives having the following Formula:

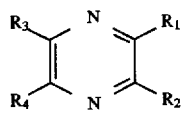

wherein $R_1$, $R_2$, $R_3$ and $R_4$ are —H, —CN, —OH, —SH, —COOH or —CONH$_2$; and whereby the pH of the lytic reagent composition ranges from 2 to 10; and further comprising the steps of:

counting the number of leukocytes in said blood sample on an automated blood analyzer utilizing DC impedance measurement;

differentiating leukocyte subpopulations according to a population distribution histogram; and reporting the number of leukocytes and leukocyte subpopulations.

18. A blood diluent useful for hemoglobin measurement and leukocyte counting comprising an aqueous solution of:

(I) an organic ligand in a sufficient amount to form a stable chromogen with hemoglobin and to preserve nuclei of leukocytes selected from the group consisting of:
  (a) triazole and its derivatives
  (b) tetrazole and its derivatives
  (c) alkaline metal salts of oxonic acid having the following Formula:

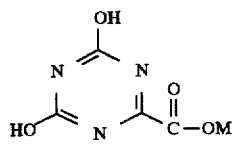

wherein M is an alkaline metal cation;
  (d) melamine

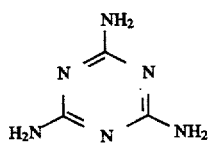

(e) aniline-2-sulfonic acid

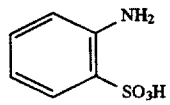

(f) quinaldic acid

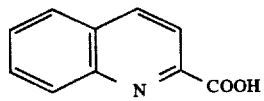

(g) 2-amino-1,3,4-thiadiazole

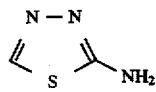

(h) triazine and its derivatives having the following Formula:

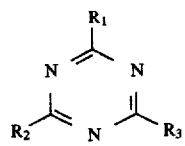

wherein $R_1$, $R_2$ and $R_3$ are —H, —OH, —SH, —COOH and heteracyclic derivatives of triazine;
  (i) urazole

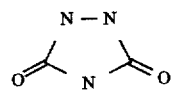

(g) DL-pipecolinic acid

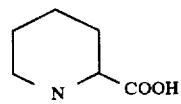

(k) isonicotinamide

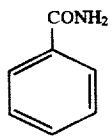

(l) anthranilonitrile

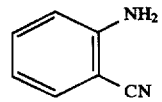

(m) 6-aza-2-thiothymine

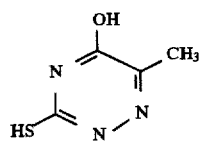

(n) adenine

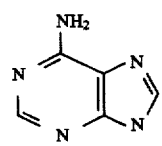

(o) 3-(2-thienyl)acrylic acid

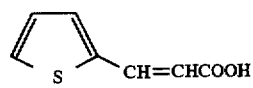

(p) benzoic acid, or alkali metal and ammonium salts of benzoic acid having the following Formula:

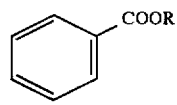

wherein R is —H, NH$_4^+$ or alkali metal cations; and (q) pyrazine and its derivatives having the following Formula:

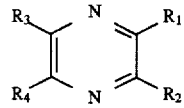

wherein R$_1$, R$_2$ R$_3$ and R$_4$ are —H, —CN, —OH, —SH, —COOH or —CONH$_2$; and (II) a salt or salts to adjust an osmolality of the diluent to approximately 250 to 400 mOsm.

19. The diluent of claim 18 wherein the organic ligand has concentrations in a range of about 0.5 g/L to about 20 g/L.

20. A method of analyzing blood to determine hemoglobin concentration of a blood sample comprising:

(a) diluting a blood sample with the blood diluent of claim 18;

(b) mixing the diluted blood sample with a lytic reagent to lyse erythrocytes and to form a stable hemoglobin chromogen;

(c) measuring absorbance of the formed hemoglobin chromogen at a predetermined wavelength;

(d) determining total hemoglobin concentration of said blood sample from the measured absorbance of the hemoglobin chromogen; and (e) reporting the total hemoglobin concentration of said blood sample.

21. A method of analyzing blood to determine the number of leukocytes in a blood sample comprising:

(a) diluting a blood sample with the blood diluent of claim 18;

(b) mixing the diluted blood sample with a lytic reagent to lyse erythrocytes and to preserve nuclear volume of leukocytes;

(c) counting the leukocytes in an automated blood analyzer utilizing DC impedance measurement; and (d) reporting the number of leukocytes in said blood sample.

22. A method for hemoglobin measurement and differential counting of leukocyte subpopulations comprising:

(1) diluting a blood sample with a blood diluent composition comprising an aqueous solution of:

(I) an organic ligand in a sufficient amount to form a stable chromogen with hemoglobin selected from the group consisting of:

(a) triazole and its derivatives
(b) melamine

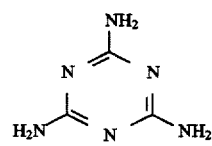

(c) 2-amino-1,3,4-thiadiazole $$\underset{S}{\overset{N-N}{\diagup\!\!\!\diagdown}}\text{—NH}_2$$

(d) triazine and its derivatives having the following Formula:

$$\underset{R_2\ \ N\ \ R_3}{\overset{R_1}{\diagdown\!\!\!N\diagup\!\!\!N}}$$

wherein R$_1$, R$_2$ and R$_3$ are —H, —OH, —SH, —COOH and heteracyclic derivatives of triazine;

(e) DL-pipecolinic acid (f) isonicotinamide; and (g) pyrazine and its derivatives having the following Formula:

wherein R$_1$, R$_2$ R$_3$ and R$_4$ are —H, —CN, —OH, —SH, —COOH or —CONH$_2$; and (II) a salt or salts to adjust an osmolality of the diluent to approximately 250 to 400 mOsm (2) mixing the diluted blood sample with a lytic reagent to lyse erythrocytes and form a stable hemoglobin chromogen, and to preserve nuclear volumes of the leukocyte subpopulations;

(3) counting leukocytes in the blood sample on an automated blood analyzer utilizing DC impedance measurement and measuring absorbance of the formed hemogolbin chromogen at a predetermined wavelength;

(4) calculating total hemoglobin concentration of said sample from the measured absorbance;

(5) differentiating leukocyte subpopulations according to a population distribution histogram; and (6) reporting the number of leukocytes and the number of leukocyte subpopulations.

23. The method of claim 22, wherein the leukocyte subpopulations include lymphocytes, monocytes and granulocytes.

24. The method of claim 22, wherein the organic ligand has concentrations in a range of about 0.5 g/L to about 20 g/L.

* * * * *

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

Column 14, line 30, change "HCI" to --HCl--

Column 14, line 38, change "82" to --85--

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

Please add the following claims:

25. A cyanide-free lytic reagent composition comprising an aqueous solution of:

(I) at least one surfactant in a sufficient amount to hemolyse erythrocytes and release hemoglobin for a determination of hemoglobin concentration selected from the group consisting of:

(a) quaternary ammonium salts, represented by the following molecular structure:

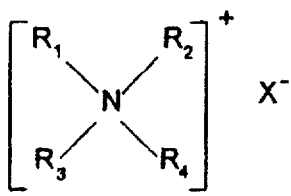

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions;

(b) pyridinium salts represented by the following molecular structure:

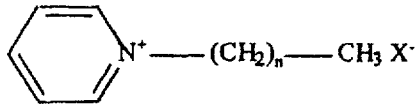

wherein n is an integer from 7 to 12 and $X^-$ is an anionic group;

(c) alkyl sulfonic acid, or alkaline metal salts of alkyl sulfonates; and

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

(d) organic phosphate esters, or alkaline metal salts of organic phosphate esters; and (II) an organic ligand in a sufficient amount to form a stable chromogen with hemoglobin selected from the group consisting of (a) triazole and its derivatives; and (b) tetrazole and its derivatives.

26. A cyanide-free lytic reagent composition comprising an aqueous solution of:

(I) at least one surfactant in a sufficient amount to hemolyse erythrocytes and release hemoglobin for a determination of hemoglobin concentration selected from the group consisting of:

(a) quaternary ammonium salts, represented by the following molecular structure:

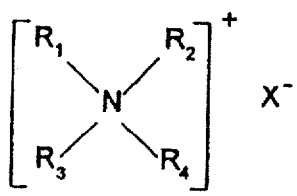

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions;

(b) pyridinium salts represented by the following molecular structure:

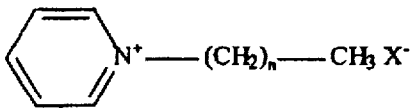

wherein n is an integer from 7 to 12 and $X^-$ is an anionic group;

(c) alkyl sulfonic acid, or alkaline metal salts of alkyl sulfonates; and (d) organic phosphate esters, or alkaline metal salts of organic phosphate esters; and (II) an organic ligand in a sufficient amount to form a stable chromogen with hemoglobin selected from the group consisting of:

(a) alkaline metal salts of oxonic acid having the following formula:

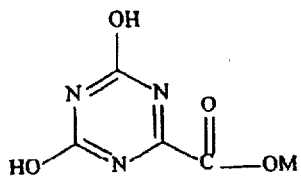

UNITED STATES PATENT AND TRADEMARK OFFICE
CERTIFICATE OF CORRECTION

PATENT NO.  : 5,763,280
DATED       : Jun. 9, 1998
INVENTOR(S) : Yi Li, et al

It is certified that error appears in the above-indentified patent and that said Letters Patent is hereby corrected as shown below:

wherein M is an alkaline metal cation;

(b)    melamine

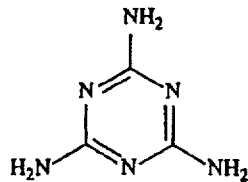

(c)    aniline-2-sulfonic acid; and

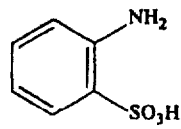

(d)    quinaldic acid.

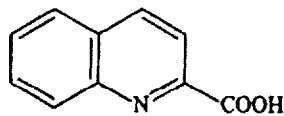

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

27. A cyanide-free lytic reagent composition comprising an aqueous solution of:

(I) at least one surfactant in a sufficient amount to hemolyse erythrocytes and release hemoglobin for a determination of hemoglobin concentration selected from the group consisting of:

(a) quaternary ammonium salts, represented by the following molecular structure:

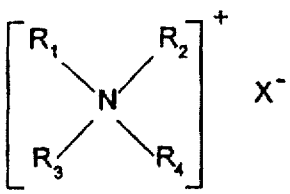

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anions;

(b) pyridinium salts represented by the following molecular structure:

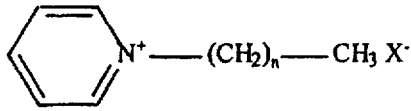

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

wherein n is an integer from 7 to 12 and X⁻ is an anionic group;

(c)    alkyl sulfonic acid, or alkaline metal salts of alkyl sulfonates; and (d)    organic phosphate esters, or alkaline metal salts of organic phosphate esters; and (II)    an organic ligand in a sufficient amount to form a stable chromogen with hemoglobin selected from the group consisting of:

(a)    2-amino-1,3,4-thiadiazole

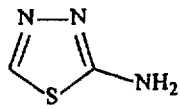

(b)    triazine and its derivatives having the following formula:

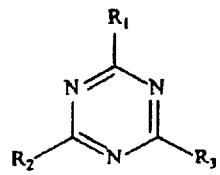

wherein $R_1$, $R_2$ and $R_3$ are -H, -OH, -SH, -COOH and heteracyclic derivatives of triazine;

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-indentified patent and that said Letters Patent is hereby corrected as shown below:

(c)  urazole

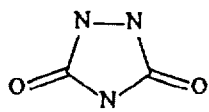

(d)  DL-pipecolinic acid

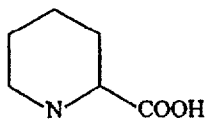

(e)  isonicotinamide

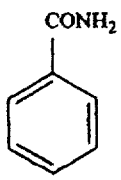

(f)  anthranilonitrile

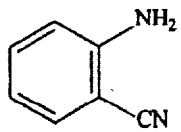

UNITED STATES PATENT AND TRADEMARK OFFICE
CERTIFICATE OF CORRECTION

PATENT NO. : 5,763,280　　　　　　　　　　　　　　　　Page 9 of 10
DATED     : Jun. 9, 1998
INVENTOR(S) : Yi Li, et al It is certified that error appears in the above-indentified patent and that said Letters Patent is hereby corrected as shown below:

(g)　　6-aza-2-thiothymine

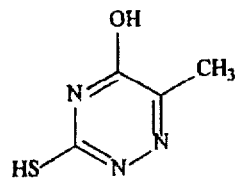

(h)　　adenine

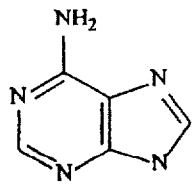

(i)　　3-(2-thienyl)acrylic acid

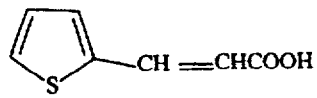

UNITED STATES PATENT AND TRADEMARK OFFICE
CERTIFICATE OF CORRECTION

PATENT NO. : 5,763,280
DATED : Jun. 9, 1998
INVENTOR(S) : Yi Li, et al

It is certified that error appears in the above-identified patent and that said Letters Patent is hereby corrected as shown below:

(j) benzoic acid, or alkali metal and ammonium salts of benzoic acid having the following formula:

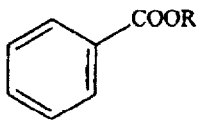

wherein R is -H, $NH_4^+$ or alkali metal cations; and (k) pyrazine and its derivatives having the following formula:

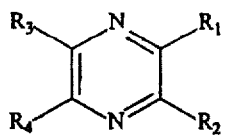

wherein $R_1$, $R_2$ $R_3$ and $R_4$ are -H, -CN, -OH, -SH, -COOH or -CONH$_2$.

Signed and Sealed this

Twenty-ninth Day of September, 1998

Attest:

BRUCE LEHMAN

*Attesting Officer*     *Commissioner of Patents and Trademarks*